US012502205B2

(12) United States Patent
Amiot et al.

(10) Patent No.: US 12,502,205 B2
(45) Date of Patent: *Dec. 23, 2025

(54) DEVICE AND SURGICAL TECHNIQUE FOR FOOT SURGERY

(71) Applicant: RELJA Innovations, Inc., Wauwatosa, WI (US)

(72) Inventors: Robby A. Amiot, Brookfield, WI (US); Jacob Flagle, Indianapolis, IN (US)

(73) Assignee: RELJA Innovations, Inc., Wauwatosa, WI (US)

( * ) Notice: Subject to any disclaimer, the term of this patent is extended or adjusted under 35 U.S.C. 154(b) by 111 days.

This patent is subject to a terminal disclaimer.

(21) Appl. No.: 18/396,897

(22) Filed: Dec. 27, 2023

(65) Prior Publication Data

US 2024/0122623 A1 Apr. 18, 2024

Related U.S. Application Data

(63) Continuation-in-part of application No. 17/980,756, filed on Nov. 4, 2022, now Pat. No. 11,883,075.

(Continued)

(51) Int. Cl.
*A61B 17/56* (2006.01)

(52) U.S. Cl.
CPC ........ *A61B 17/56* (2013.01); *A61B 2017/565* (2013.01)

(58) Field of Classification Search
CPC ..... A61B 17/56; A61B 17/66; A61B 17/6466; A61B 17/846; A61B 2017/565; A61B 90/90

(Continued)

(56) References Cited

U.S. PATENT DOCUMENTS 6,391,031 B1 5/2002 Toomey
7,749,278 B2 7/2010 Frederick et al.

(Continued)

FOREIGN PATENT DOCUMENTS

DE 102008004922 A1 7/2009
WO 2020139938 A1 7/2020

(Continued)

OTHER PUBLICATIONS

International Search Report for Application No. PCT/US2020/064002 dated Apr. 28, 2021 (4 pages).

*Primary Examiner* — Eduardo C Robert
*Assistant Examiner* — David C Comstock
(74) *Attorney, Agent, or Firm* — Wong Meyer Smith & McConnell

(57) ABSTRACT

A correction clamp assembly that permits a physician to surgically correct a bunion or similar deformity is provided. The assembly includes an elongate bridge, as well as first and second blocks slidably or rotatably connected to the elongate bridge. More specifically, first block is configured to slide along a slot formed in the elongate bridge, as well as rotate relative thereto. Additionally, the second block is configured to rotate relative to the elongate bridge. First and second pins may be configured to extend through the first and second block, and then into various pieces of bone. Once a cut is made in a portion of joint or bone, the pins can thereafter be moved towards and away from one another to position the respective pieces of bone in a desired location. Locking screws may also be provided to releasably secure the blocks relative to the bridge.

7 Claims, 23 Drawing Sheets

Related U.S. Application Data

(60) Provisional application No. 63/276,876, filed on Nov. 8, 2021, provisional application No. 63/309,858, filed on Feb. 14, 2022.

(58) Field of Classification Search
USPC ................................ 606/59, 329, 82, 87, 96
See application file for complete search history.

(56) References Cited

U.S. PATENT DOCUMENTS

| | | | |
|---|---|---|---|
| 8,021,367 | B2 | 9/2011 | Bourke et al. |
| 8,425,554 | B2 | 4/2013 | Denove et al. |
| 8,545,501 | B2 | 10/2013 | Wong |
| D695,402 | S | 12/2013 | Dacosta et al. |
| 8,828,063 | B2 | 9/2014 | Blitz et al. |
| D720,456 | S | 12/2014 | Dacosta et al. |
| 8,992,532 | B2 | 3/2015 | Wong |
| 9,044,250 | B2 | 6/2015 | Olsen et al. |
| 9,060,822 | B2 | 6/2015 | Lewis et al. |
| 9,107,715 | B2 | 8/2015 | Blitz et al. |
| 9,204,874 | B2 | 12/2015 | Denove et al. |
| 9,814,474 | B2 | 11/2017 | Montoya et al. |
| 9,907,558 | B2 | 3/2018 | Fallin et al. |
| 9,918,854 | B2 | 3/2018 | Bonin, Jr. et al. |
| 9,949,744 | B2 | 4/2018 | McCormick |
| 10,039,559 | B2 | 8/2018 | Awtrey et al. |
| 10,045,862 | B2 | 8/2018 | Wong |
| 10,245,086 | B2 | 4/2019 | Treace et al. |
| 10,342,529 | B2 | 7/2019 | Fallin et al. |
| D860,456 | S | 9/2019 | Buchanan et al. |
| 10,463,407 | B2 | 11/2019 | Taylor et al. |
| 10,512,470 | B1 | 12/2019 | Bays et al. |
| 10,524,808 | B1 | 1/2020 | Hissong et al. |
| 10,575,862 | B2 | 3/2020 | Bays et al. |
| 10,582,936 | B1 | 3/2020 | Hissong et al. |
| 10,610,241 | B2 | 4/2020 | Wagner et al. |
| 10,646,263 | B2 | 5/2020 | Lamm et al. |
| 10,653,432 | B2 | 5/2020 | Luttrell et al. |
| 10,653,465 | B2 | 5/2020 | Blacklidge |
| 10,653,467 | B2 | 5/2020 | Brumfield et al. |
| 10,682,168 | B2 | 6/2020 | Kay et al. |
| 10,736,641 | B2 | 8/2020 | Fallin et al. |
| 10,736,645 | B2 | 8/2020 | McCormick |
| 10,786,291 | B2 | 9/2020 | Weiner et al. |
| 10,881,436 | B2 | 1/2021 | Muller et al. |
| 10,888,335 | B2 | 1/2021 | Dayton et al. |
| 10,888,340 | B2 | 1/2021 | Awtrey et al. |
| 10,888,365 | B2 | 1/2021 | Tyber et al. |
| 11,000,298 | B1 | 5/2021 | Graziano |
| 11,007,068 | B2 | 5/2021 | Wong |
| 11,033,304 | B2 | 6/2021 | Blacklidge |
| 11,039,873 | B2 | 6/2021 | Santrock et al. |
| 11,051,831 | B2 | 7/2021 | Luttrell et al. |
| 11,076,863 | B1 | 8/2021 | Bays et al. |
| 11,147,590 | B2 | 10/2021 | Dayton et al. |
| 11,229,443 | B2 | 1/2022 | Wong et al. |
| 11,246,588 | B2 | 2/2022 | Maclure et al. |
| 11,304,735 | B2 | 4/2022 | Sayger et al. |
| 11,317,954 | B2 | 5/2022 | Nachtrab et al. |
| 11,324,497 | B2 | 5/2022 | Isch et al. |
| 11,889,998 | B1 * | 2/2024 | Treace ................. A61B 17/685 |
| 2004/0097944 | A1 * | 5/2004 | Koman .............. A61B 17/6425 606/55 |
| 2013/0231668 | A1 | 9/2013 | Olsen et al. |
| 2016/0324532 | A1 | 11/2016 | Montoya et al. |
| 2017/0079701 | A1 | 3/2017 | Geldwert |
| 2017/0164989 | A1 | 6/2017 | Weiner et al. |
| 2018/0110530 | A1 | 4/2018 | Wagner |
| 2018/0250024 | A1 | 9/2018 | Woodard et al. |
| 2019/0125418 | A1 | 5/2019 | Muller et al. |
| 2019/0175237 | A1 | 6/2019 | Treace et al. |
| 2019/0307495 | A1 | 10/2019 | Geldwert |
| 2020/0046412 | A1 | 2/2020 | Nachtrab et al. |
| 2020/0054374 | A1 | 2/2020 | Schumacher et al. |
| 2020/0060697 | A1 | 2/2020 | Nachtrab et al. |
| 2020/0060739 | A1 | 2/2020 | Nachtrab et al. |
| 2020/0069334 | A1 * | 3/2020 | Moradi .............. A61B 17/6425 |
| 2020/0129304 | A1 | 4/2020 | Korman et al. |
| 2020/0170655 | A1 | 6/2020 | Zakhary et al. |
| 2020/0205844 | A1 | 7/2020 | Hissong et al. |
| 2020/0229828 | A1 | 7/2020 | Wagner et al. |
| 2020/0261128 | A1 | 8/2020 | Kay et al. |
| 2020/0275959 | A1 | 9/2020 | Brumfield et al. |
| 2021/0045756 | A1 | 2/2021 | Zakhary et al. |
| 2021/0077120 | A1 | 3/2021 | Hatch et al. |
| 2021/0077162 | A1 | 3/2021 | Muller et al. |
| 2021/0085346 | A1 | 3/2021 | Awtrey et al. |
| 2021/0106372 | A1 | 4/2021 | Tyber et al. |
| 2021/0196324 | A1 * | 7/2021 | Dayton .................. A61B 17/66 |
| 2021/0228381 | A1 | 7/2021 | Wong |
| 2021/0259716 | A1 | 8/2021 | Woodard et al. |
| 2021/0267649 | A1 | 9/2021 | Blacklidge |
| 2021/0282823 | A1 | 9/2021 | Day et al. |
| 2021/0290251 | A1 | 9/2021 | Luttrell et al. |
| 2021/0330335 | A1 * | 10/2021 | Boffeli ................. A61B 17/151 |
| 2021/0361294 | A1 | 11/2021 | Bays et al. |
| 2022/0008106 | A1 | 1/2022 | Ellington |
| 2022/0039816 | A1 | 2/2022 | Bruse |

FOREIGN PATENT DOCUMENTS

| | | | |
|---|---|---|---|
| WO | 2020172451 | A1 | 8/2020 |
| WO | 2021126326 | A1 | 6/2021 |
| WO | 2021158738 | A1 | 8/2021 |
| WO | 2021162805 | A1 | 8/2021 |
| WO | 20211167992 | A1 | 8/2021 |
| WO | 2021173931 | A1 | 9/2021 |
| WO | 2021206905 | A1 | 10/2021 |
| WO | 2021211249 | A1 | 10/2021 |
| WO | 2021212131 | A1 | 10/2021 |

* cited by examiner

DEVICE AND SURGICAL TECHNIQUE FOR FOOT SURGERY

CROSS-REFERENCE TO RELATED APPLICATION

The present application is a continuation-in-part application claiming priority to U.S. Non-Provisional patent application Ser. No. 17/980,756, filed on Nov. 4, 2022 and entitled Device and Surgical Technique for Foot Surgery, which claims priority on U.S. Provisional Patent Application Ser. No. 63/276,876, filed Nov. 8, 2021 and entitled Device and Surgical Technique for Foot Surgery, and U.S. Provisional Patent Application Ser. No. 63/309,858, filed on Feb. 14, 2022 and entitled Device and Surgical Technique for Foot Surgery, the entirety of both of which are hereby incorporated herein by reference.

BACKGROUND OF THE INVENTION

1. Field of the Invention

The present invention relates in general to the field of surgery. More particularly, the present invention relates to an orthopedic implant, surgical instruments for use and delivery of the implant, surgical instruments for creation of an osteotomy and/or joint fusion, and the surgical technique used with these items. Even more specifically, the present invention is directed to a corrective clamp device used during a surgical procedure. Additionally, the invention includes some or all of the following plus their combination: a correction clamp, one or more Pins, a screwdriver, one or more orthopedic implants, a drill bit, one or more tissue retractors, and a kit or kits for maintaining the components sterile. In addition, the invention also includes a method of use of the devices in a surgical procedure.

2. Discussion of the Related Art

An osteotomy and/or joint fusion is a surgical procedure that involves cutting, reshaping, or removing bone. Osteotomies and/or joint fusions are usually performed to correct a deformity in the bone. One common deformity that can be repaired by surgery is hallux valgus, also known as a bunion. Hallux valgus is a foot deformity that causes functional disability and pain and involves misalignment of the first metatarsal and phalanx.

Hallux Valgus can be repaired in a variety of ways; however one particular method involves structurally relocating the hallux and first metatarsal from a deformed position to its natural position. This technique is frequently called a Lapidus bunionectomy and/or first metatarsal cuneiform joint fusion, which involves manipulating the hallux and first metatarsal in multiple planes to correct the deformity, and then fixing it in place in the proper position to heal. Frequently, it is necessary to temporarily hold the bones in a corrected position, against the resistance of soft tissue, while they are fixated for permanent correction. It can be challenging for a physician to hold the deformed first metatarsal in its correct position and apply temporary fixation at the same time.

In addition, surgical correction frequently involves cutting bone, removing cartilage and bone, realigning or shifting the bones to the proper anatomical configuration, and then fixing the bones in the new positions such that they heal. Fixation of the bones can occur with the use of orthopedic screws, shape memory implants, or plates and screws. The surgery frequently requires incisions in the skin and soft tissues and then subsequent cutting and drilling of bone. Many conventional systems for surgery of this type require extensive dissection of soft tissue such that the physician can see the underlying bone. Extensive dissection such as this can limit or damage blood flow to the affected area and slow healing. Extensive dissection of soft tissue also risks penetrating the area around a joint, potentially permanently compromising proper joint motion. Soft tissue dissection can also damage nerves, increase swelling, or increase post-surgical pain.

Therefore, during surgery of this type, it is frequently an objective of the surgeon to avoid unnecessary disruption of tissue. This can be accomplished by both careful surgical techniques, as well as specially designed instruments and implants that minimize unnecessary tissue disruption. In particular, guides, tools, and other devices can assist a physician in accomplishing surgery, such as Lapidus bunionectomy, with less tissue dissection. A medical device system that is designed to assist the surgeon in minimizing unnecessary disruption of tissue can be described as "minimally or less invasive surgery".

Accordingly, what is needed is a medical device system that includes instruments, implants, and a surgical technique that work together to allow motion and temporary fixation of bones while also avoiding unnecessary disruption of tissue and while producing a successful surgical outcome. For instance, what is needed is a surgical clamp that allows for an attachment to the deformed first metatarsal and a second attachment to another part of the foot, and mechanisms for moving and temporarily holding the bones while the surgeon completes the procedure. What is further needed are medical devices and processes that solves the problem outlined above associated with large incisions and variable surgical results. What is further needed is an apparatus and method of use resulting in less soft tissue disruption and providing specific guided steps for the surgery. What is also needed is a corrective clamp or other device that allows for simplified, corrective reduction of the deformity and fixation of bones relative to one another. The corrective clamp allows surgeons to correct deformity in multiple planes and hold the position while permanent fixation is applied. The corrective clamp also allows surgeons to complete this without any incisions and in a timely fashion in comparison to other corrective devices of the prior art.

SUMMARY AND OBJECTS OF THE INVENTION

In accordance with a first aspect of the invention, a correction clamp assembly is provided that allows for the manipulation of first and second pieces of bone relative to one another while creating an osteotomy and/or joint fusion. The assembly includes an elongate bridge, a first block, a second block, and a plurality of pins. The elongate bridge includes a body, a first opening formed in the body, and a slot extending along and through a portion of the body. The first block is slidably and rotatably connected to the elongate bridge, for instance about the slot. The second block is rotatably connect to the elongate bridge, for instance about the first opening. The plurality of pins may include a first pin associated with the first block and a second pin associated with the second block. Additionally, the assembly may include at least one first block locking screw that is configured to releasably secure the first block relative to the elongate bridge in a lateral and rotational direction, as well as at least one second block locking screw that is configured to releasably secure the second block relative to the elongate bridge in a rotational direction. The first block may further include at least one guide rail that is configured to guide movement of the first block relative to the elongate bridge.

According to another aspect of the invention, the first pin is configured to be secured to a first metatarsal and the second pin is configured to be secured to a second metatarsal. The second pin may be configured to be manipulated in order to move the first metatarsal towards the second metatarsal.

According to yet another aspect of the present invention, the first block further comprises a main body, a tube with a first opening extending therethrough along a first axis, and a second opening extending through the body along a second axis. The second opening may be configured to receive at least one locking screw. Additionally, the second block further comprises a main body, a tube with a first opening extending therethrough along a first axis, and a second opening extending through the body along a second axis. Again, the second opening may be configured to receive at least one locking screw.

According to another aspect of the invention, the first block may also include a gripping section and an identifier. Similarly, the second block may include a gripping section and an identifier. Further still, the elongate bridge includes first and second identifiers. The first block identifier may be aligned with the first identifier of the elongate bridge, whereas the second block identifier may be aligned with the second identifier of the elongate bridge. This helps to expedite alignment and assembly of the correction clamp.

According to yet another aspect of the present invention, a method of performing a medical procedure is provided. The method includes the steps of inserting a first pin through a second metatarsal, inserting the first pin through a first block associated with a correction clamp, inserting a second pin through a first metatarsal, and inserting the second pin through a second block associated with the correction clamp. Additionally, the method may include creating a corrective cut or joint fusion position in one or more of a bone and a joint, after which the second pin may be manipulated in order to move the second block and the first metatarsal relative to the second metatarsal, for instance by pressing or pinching the second pin towards the first pin. Once a desired location is reached, the first metatarsal may be secured in place. Further, the method may include the steps of sliding the first block relative to a bridge associated with the correction clamp, and rotating the second block relative to the bridge. For instance, the first block may be slid relative to a slot formed in the bridge, while the second block may be rotated relative to a hole formed in the bridge. Additionally, the method may include sliding at least one guide rail associated with the first block to enable movement of the first block relative to the bridge. Also, the first block may be secured in place relative to the bridge using a first locking screw, whereas the second block may be secured in place relative to the bridge using a second locking screw. The method may also include the step of inserting the first pin through an opening in a tube that extends through the first block, and inserting the second pin through an opening in a tube that extends through the second block.

According to yet another aspect of the present invention, a kit for an osteotomy medical procedure is provided that includes a bridge having a body, a first opening formed in the body, and an elongate slot formed in the body, a first block configured to be secured to the bridge along the slot, and a second block configured to be secured to the bridge about the first opening, as well as a plurality of pins. The kit may also include a plurality of locking screws that are configured to releasably secure the first block and the second block in place relative to the bridge. Additionally the kit may include a cutting saw for creating a corrective cut or joint fusion in one or more of a bone and a joint, as well as a screw configured to secure a portion of the bone in place.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
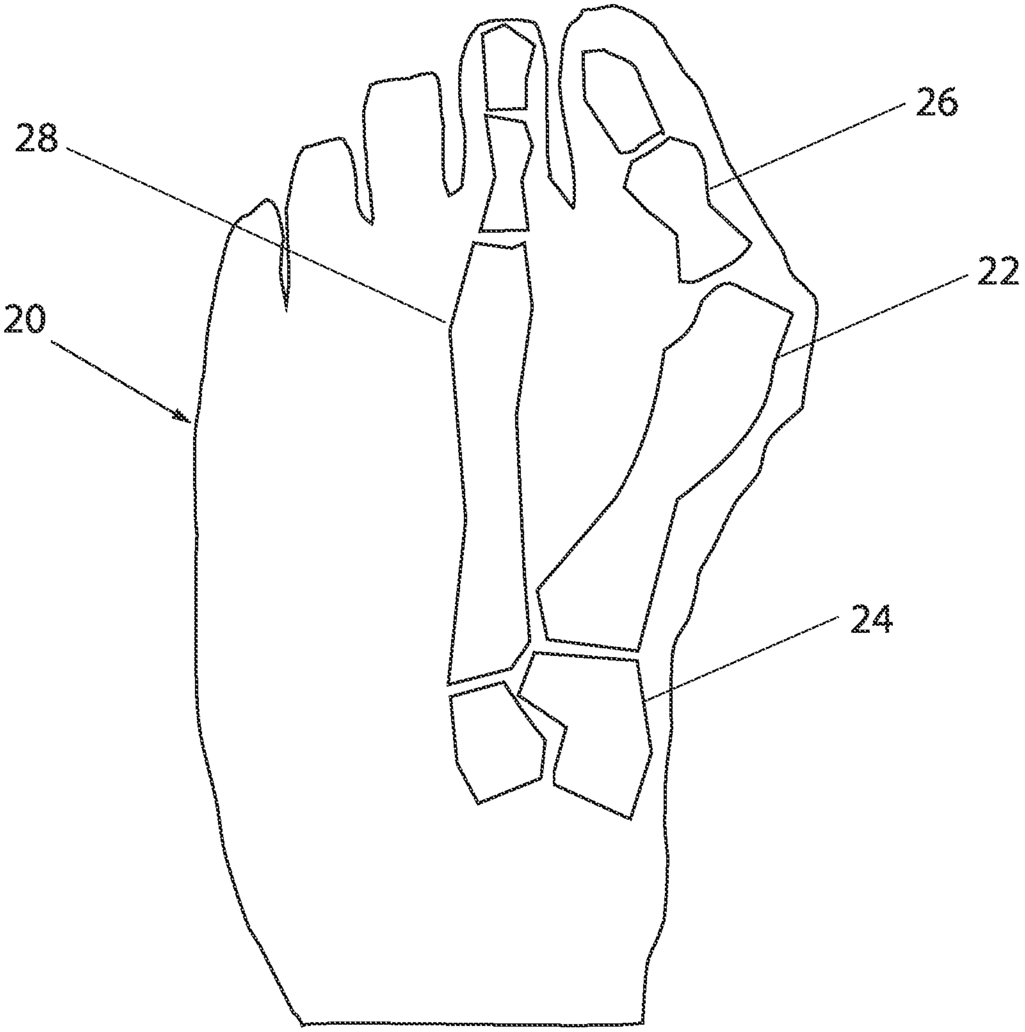
FIG. 1 is a top plan view of the bones of a foot with a bunion deformity.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DETAILED DESCRIPTION OF PREFERRED EMBODIMENTS

The present invention and the various features and advantageous details thereof are explained more fully with reference to the non-limiting embodiments described in detail in the following description. Initially, a variety of tools will be described, after which use of the tools together will be described to perform the desired medical procedure. Preferably, the described system can be used to streamline and simplify minimally invasive surgical procedures. Additionally, the described system preferably results in better cosmetic results, such as less scarring, decreased trauma to the soft tissues, less damage to blood supply, faster healing, less time in the operating room for the patient and physicians, less post-operative pain, swelling, and complications, and/or quicker recovery time and earlier return to activities. While the description below will primarily be in relation to surgical procedures designed to correct issues relating to hallux valgus/bunions, the present invention could similarly be used to correct other issues in a patient's feet, ankles, and elsewhere on the body.

Figure 2:
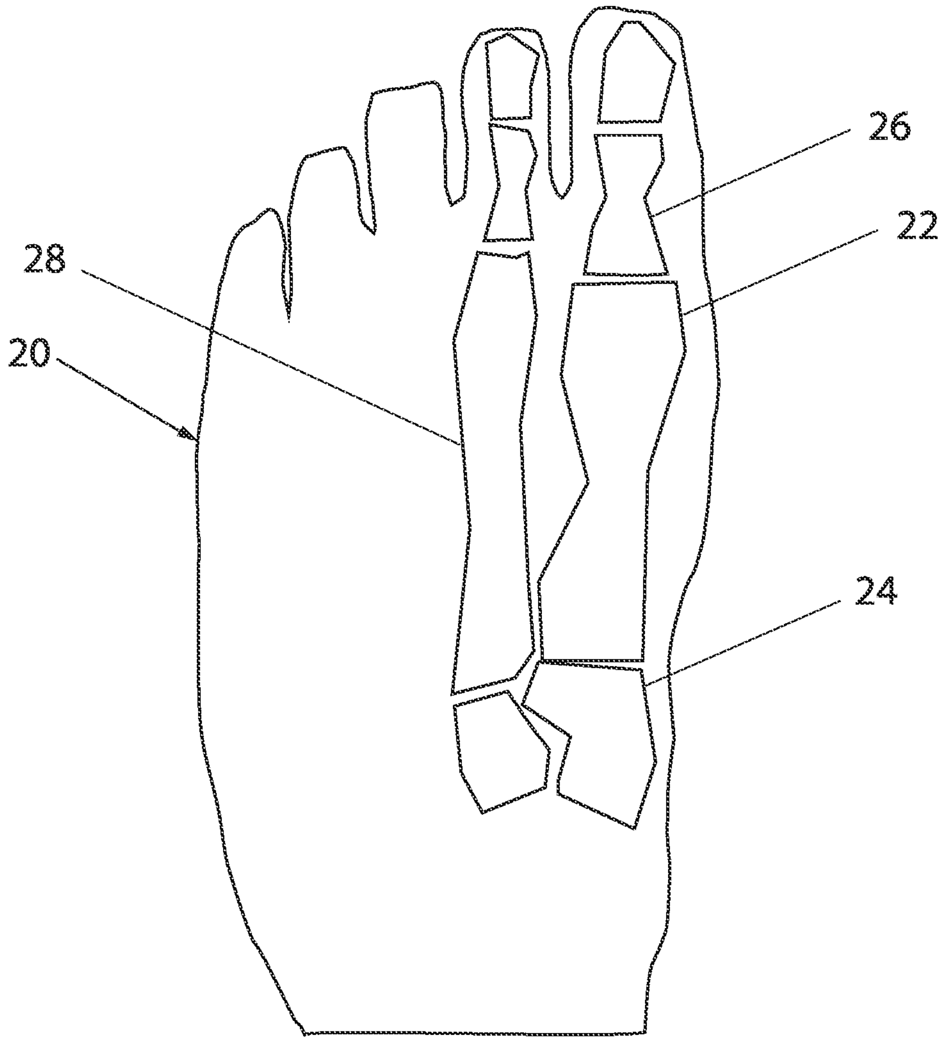
FIG. 2 s a top plan view of the bones of a foot with normal anatomy.
Figure 3:
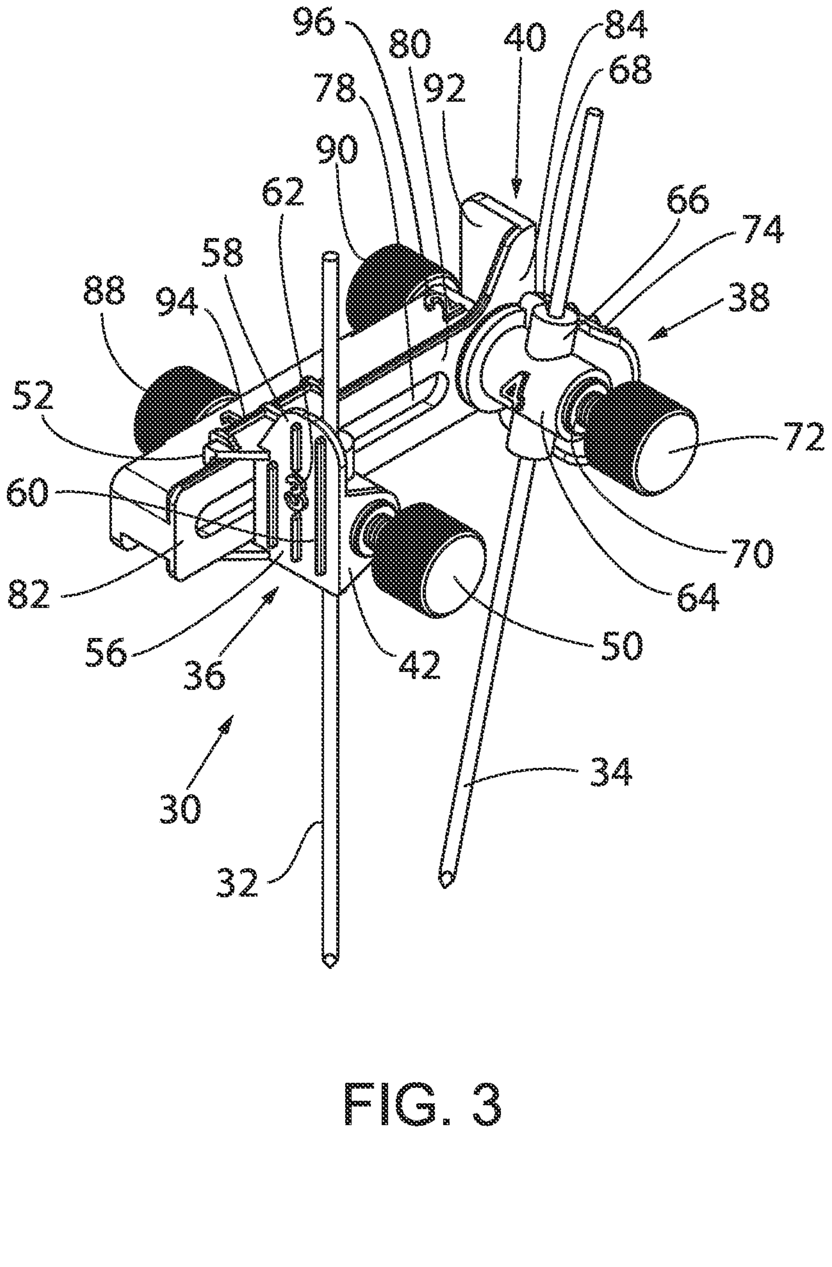
FIG. 3 is an isometric view of an inventive correction clamp device with pins extending therethrough.
Figure 4:
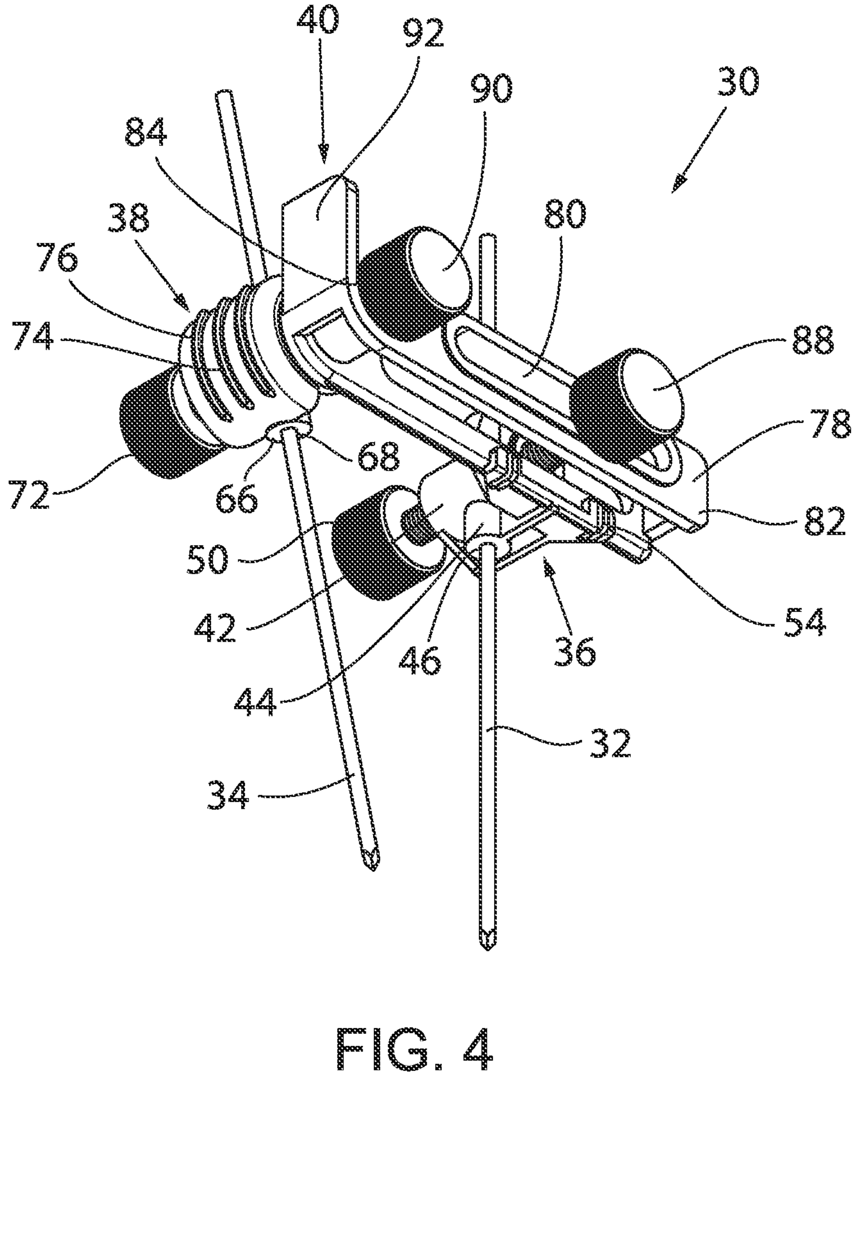
FIG. 4 is an isometric view of the correction clamp with pins of FIG. 3.
Figure 5:
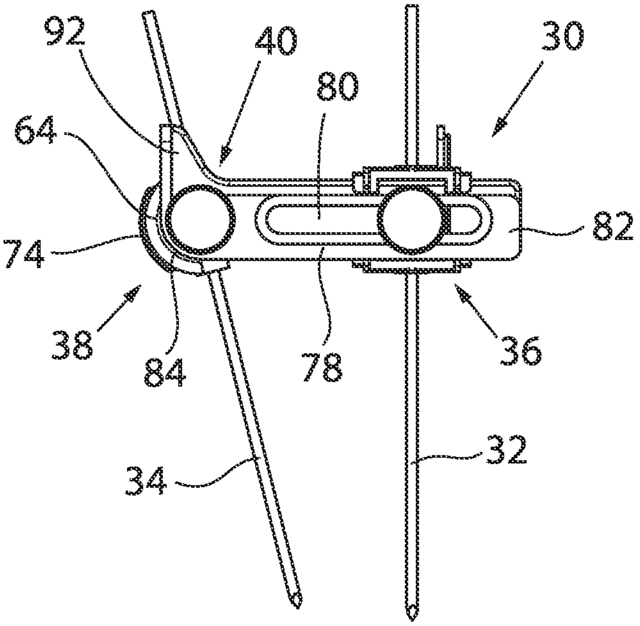
FIG. 5 is a left side elevation view of the correction clamp with pins of FIGS. 3 and 4.
Figure 6:
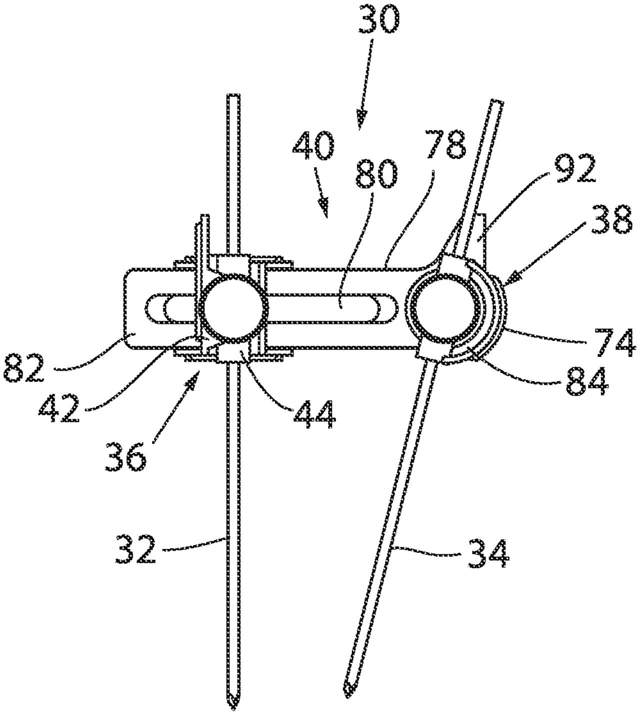
FIG. 6 is a right side elevation view of the correction clamp with pins of FIGS. 3-5.
Figure 7:
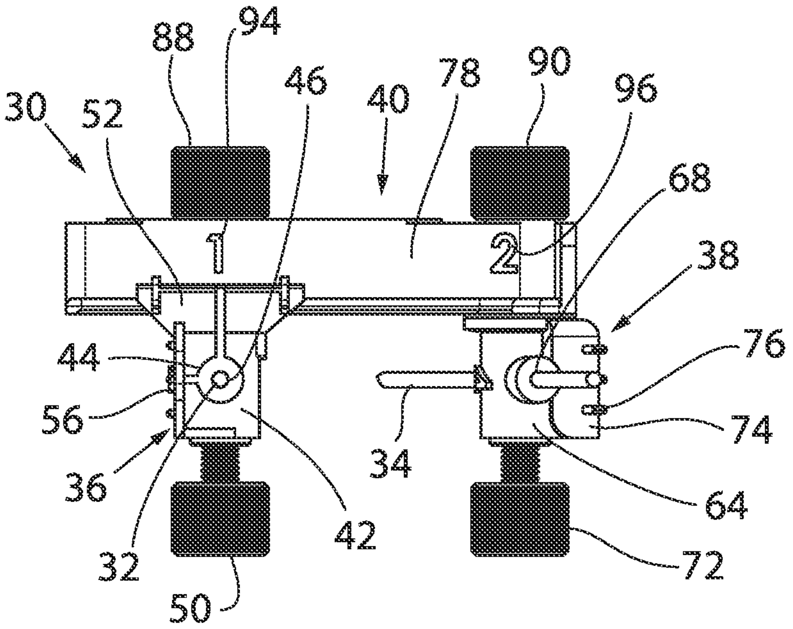
FIG. 7 is a top plan view of the correction clamp with pins of FIGS. 3-6.
Figure 8:
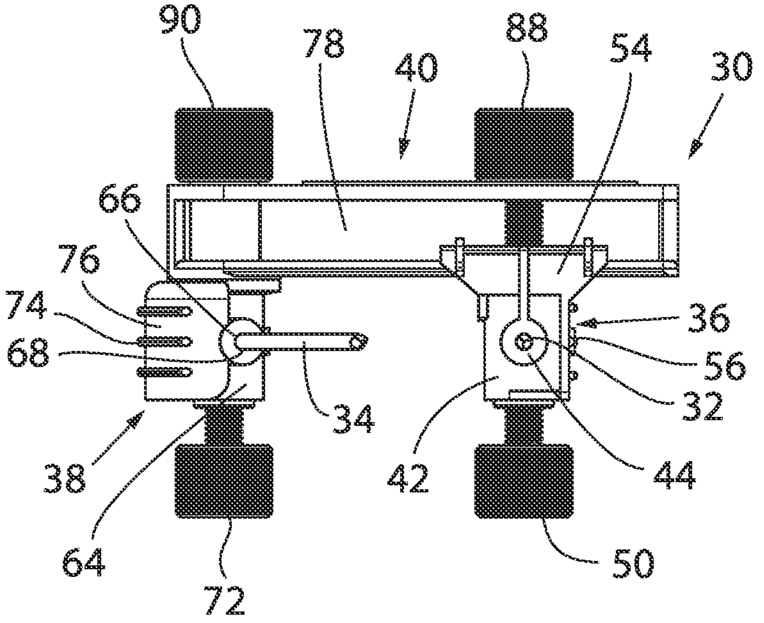
FIG. 8 is a bottom plan view of the correction clamp with pins of FIGS. 3-7.
Figure 9:
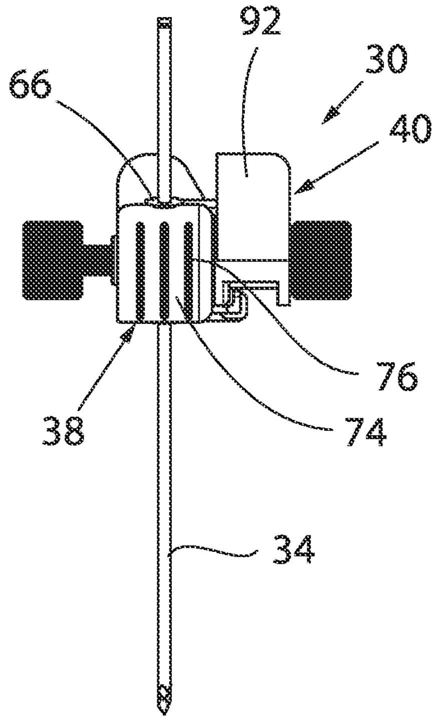
FIG. 9 is a front end elevation view of the correction clamp with pins of FIGS. 3-8.
Figure 10:
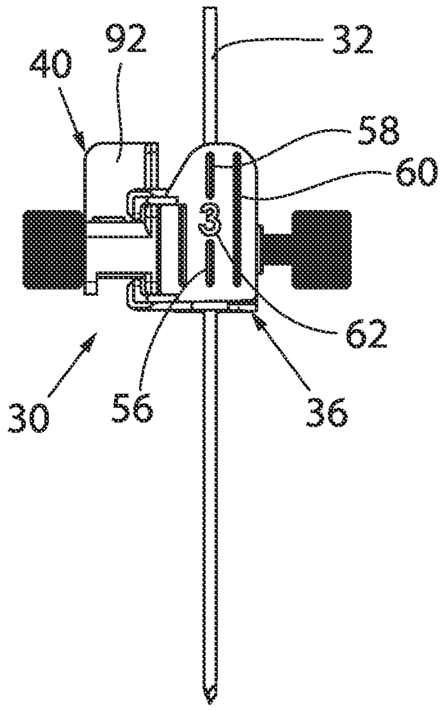
FIG. 10 is a rear end elevation view of the correction clamp with pins of FIGS. 3-9.
Figure 11:
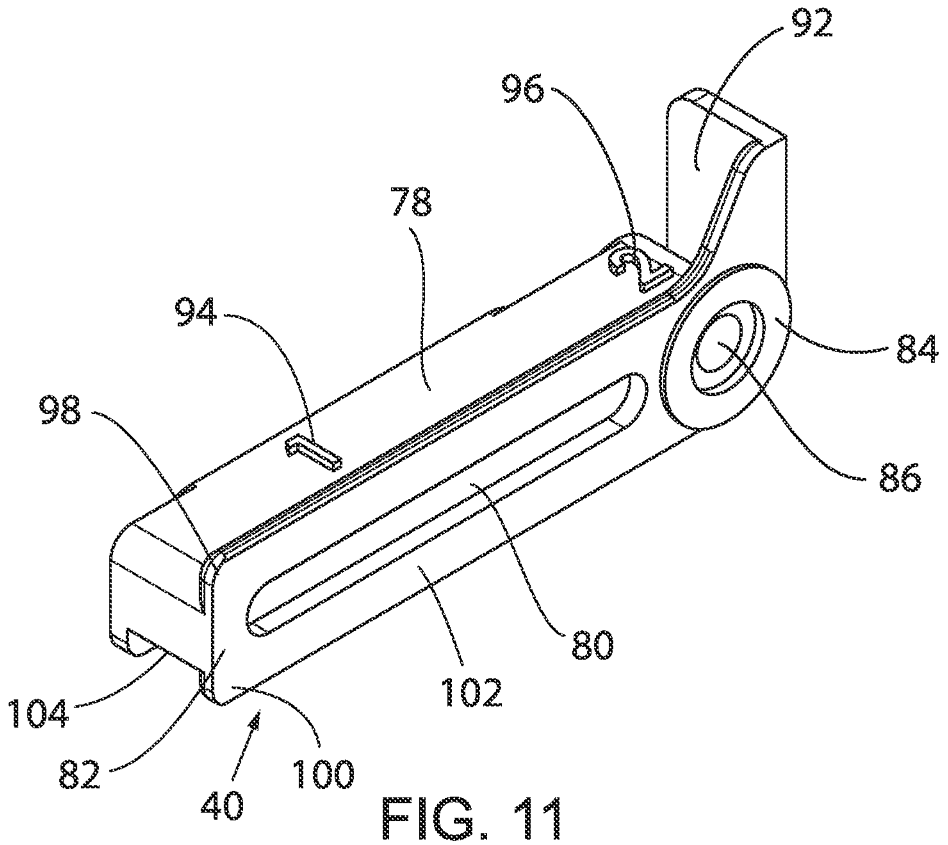
FIG. 11 is an isometric view of a bridge of the correction clamp of FIGS. 3-10.

Turning initially to FIG. 1, a foot 20 with a bunion deformity that requires surgical correction is illustrated, whereas FIG. 2 shows a normal foot with no deformity. The feet 20 in both FIGS. 1 and 2 show a second metatarsal 28 that has no or minimal deformity. As seen in FIG. 1, the first metatarsal 22 is deformed in multiple planes. Additionally, the medial cuneiform 24 and the proximal phalanx 26 are also deformed due to their attachment to the first metatarsal 22. When the present invention is used to surgically correct the foot shown in FIG. 1, the first metatarsal 22 will be substantially repositioned as it is shown in FIG. 2 into a normal anatomic position. As a result, the medial cuneiform 24 and the proximal phalanx 26 are also in the proper anatomic position.

Moving generally to FIGS. 3-13, the inventive correction clamp 30 and associated components such as a first installed pin 32 and a second installed pin 34, are illustrated. This inventive correction clamp 30 is used to remedy the bunion deformity shown in FIG. 1, after which the foot will be surgically corrected to look substantially more anatomic as it does in FIG. 2 as will further be described.

The correction clamp 30 consists of three main pieces: a first block 36, a second block 38, and a bridge 40. Each of these are shown assembled in FIGS. 3-10, and in isolation in FIGS. 11-13. Advantageously, each of the first block 36, the second block 38, and the bridge 40 are relatively simple parts have few components that can be installed and manipulated relative to one another, and can also be affordably manufactured. While exemplary embodiments of these components are shown in the figures, these components could take virtually any shape or size while functioning as described here. Further, while features of these components are described below, each of these components could include additional or fewer components depending on any number of different factors.

Figure 12:
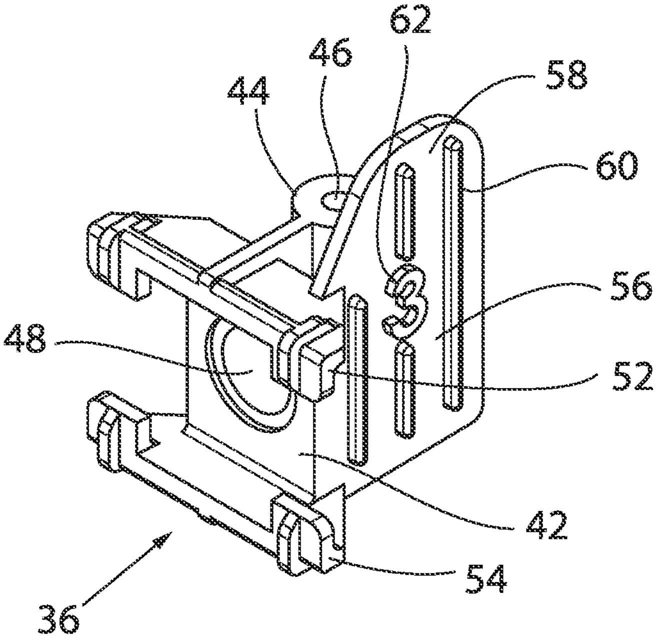
FIG. 12 is an isometric view of a first block of the correction clamp of FIGS. 3-10.

Turning to FIG. 12, the first block 36 includes a body 42 that has a tube 44 with a pin hole opening 46 formed therein that extends through the length of the tube 44. The tube 44 and the pin hole opening 46 extend along a first axis, which will be described herein as a substantially vertical axis based on how it is shown in FIG. 12, but of course the first block 36, as well as the clamp 30, could be oriented in any direction when in use. A screw hole opening 48 also extends through the body 42 of the first block 36, with the screw hole opening 48 extending along a second axis that is substantially perpendicular relative to the first axis. As shown, the second axis is substantially horizontal, such that the screw hole opening 48 extends in the horizontal direction.

The tube 44 is configured to receive the first pin 32 through the pin hole opening 46. The first pin 32 can move freely through the tube 44, otherwise, it can be locked into place, for instance using a locking screw 50 that can be inserted into the screw hole opening 48, after which it can be twisted to either release the first pin 32 or hold it in place.

Additionally, top and bottom guide rails 52, 54 are provided that extend from the body 42 of the first block 36. Again, use of the words "top" and "bottom" are used relative to what is shown in FIG. 12, although the components could be used in other orientations. These guide rails 52, 54 are configured to secure the first block 36 to the bridge 40 and enable movement of the first block 36 relative to the bridge 40 as will further be described below.

Further still, the first block 36 may include a grip section 56, which can be engaged by a user's fingers. The grip section 56 includes a tab 58, as well as a textured portion 60 that can be easily gripped by and manipulated by a user during a medical procedure. Further still, the first block 36 may include an identifier 62, here the number "3", which helps users identifying the relevant parts and assembly and/or use of the correction clamp 30. The first block 36 may not include an identifier in other embodiments.

Figure 13:
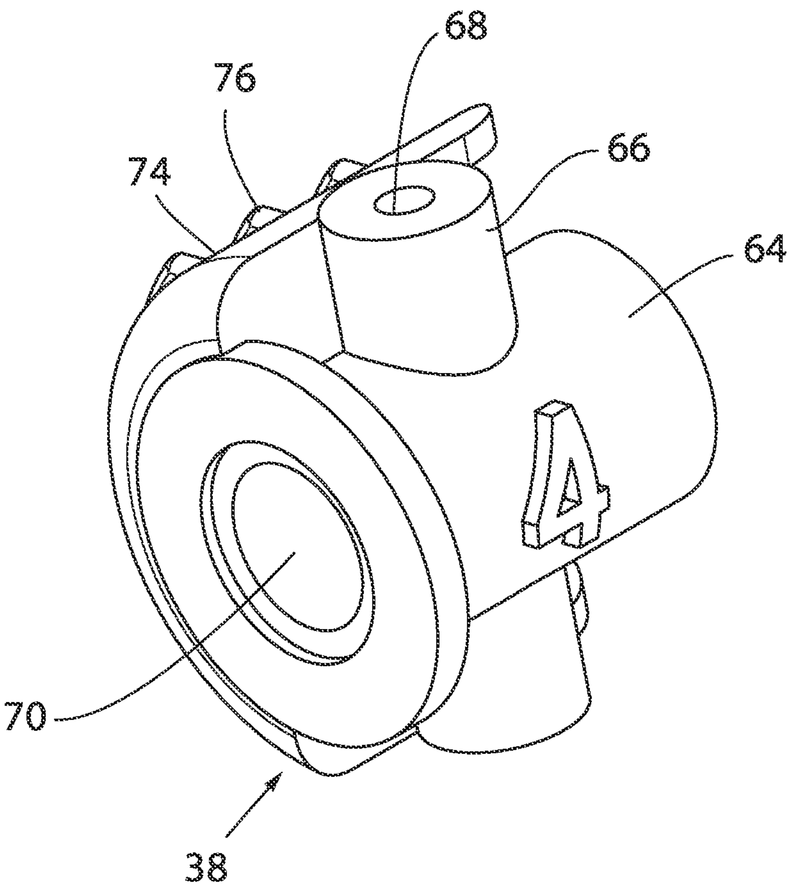
FIG. 13 is an isometric view of a second block of the correction clamp of FIGS. 3-10.
Figure 14:
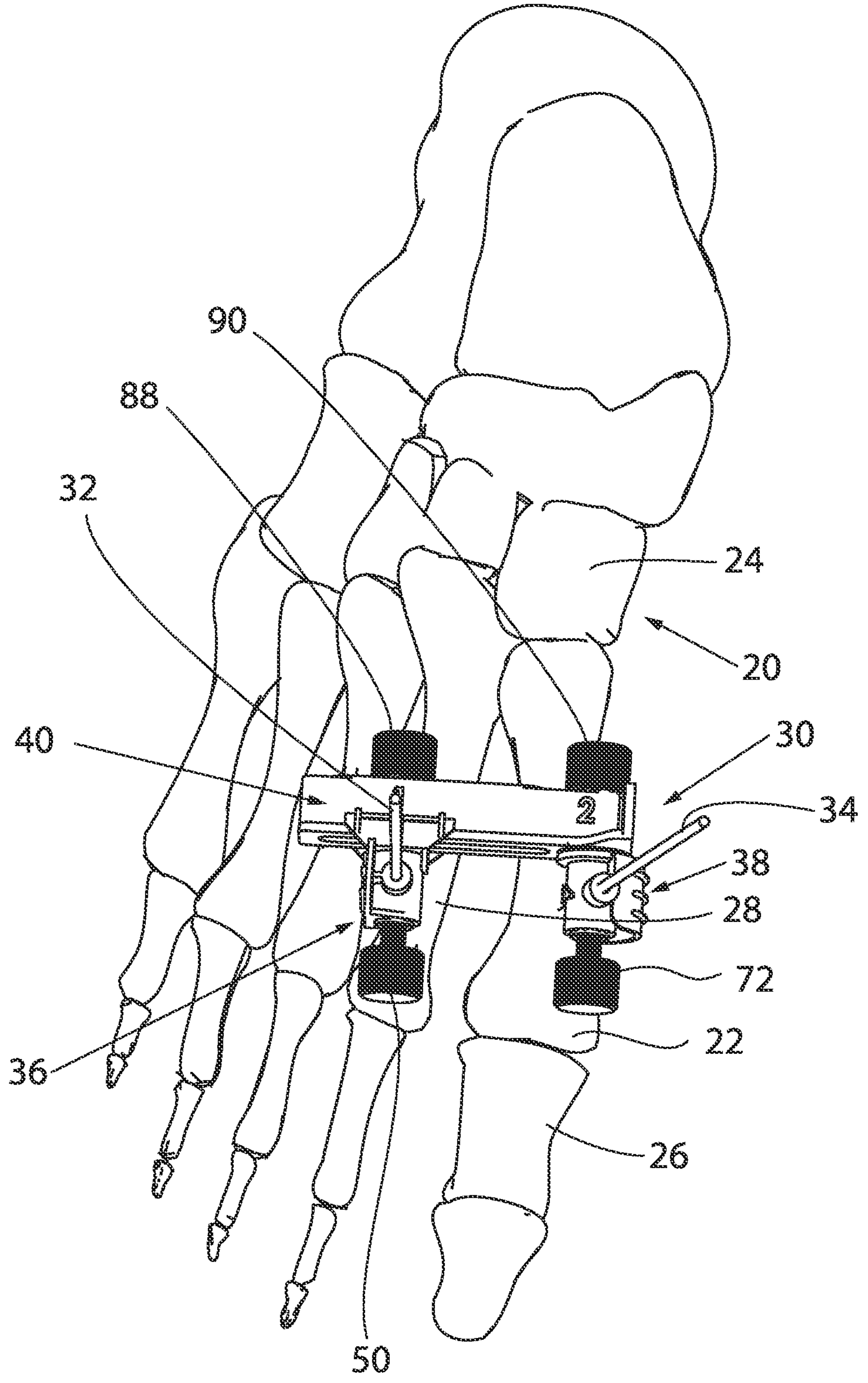
FIG. 14 is a perspective view of a first embodiment of the correction clamp positioned over a first and second metatarsal.
Figure 15:
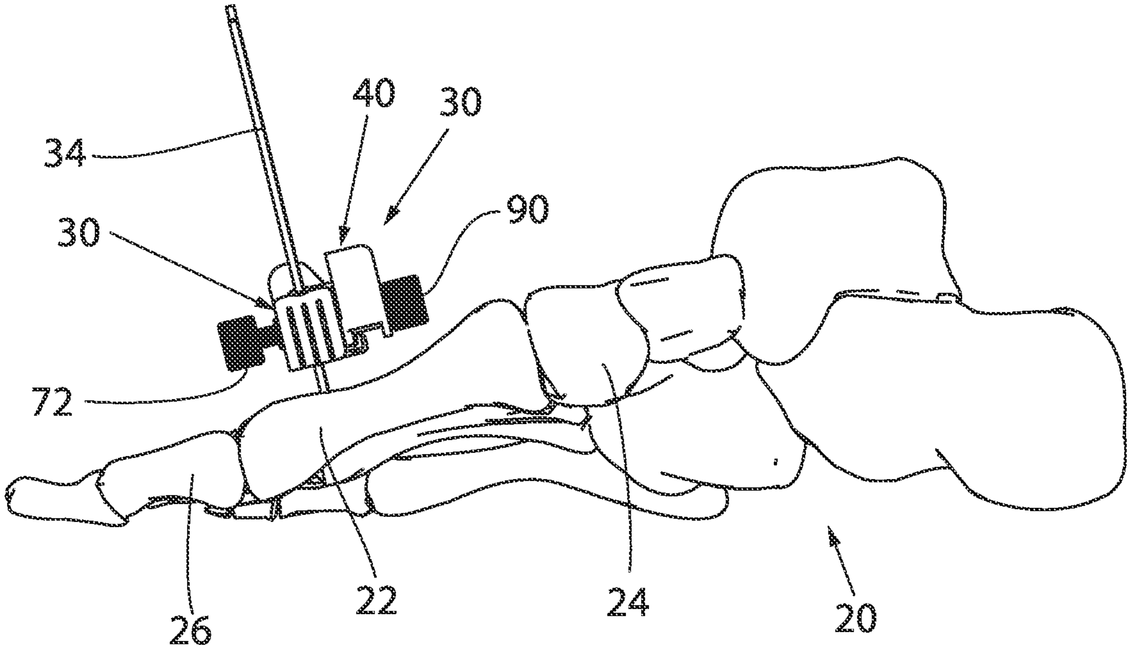
FIG. 15 is a left side elevation view of a foot with a bunion deformity, with the first embodiment of the correction clamp positioned over first and second metatarsal.
Figure 16:
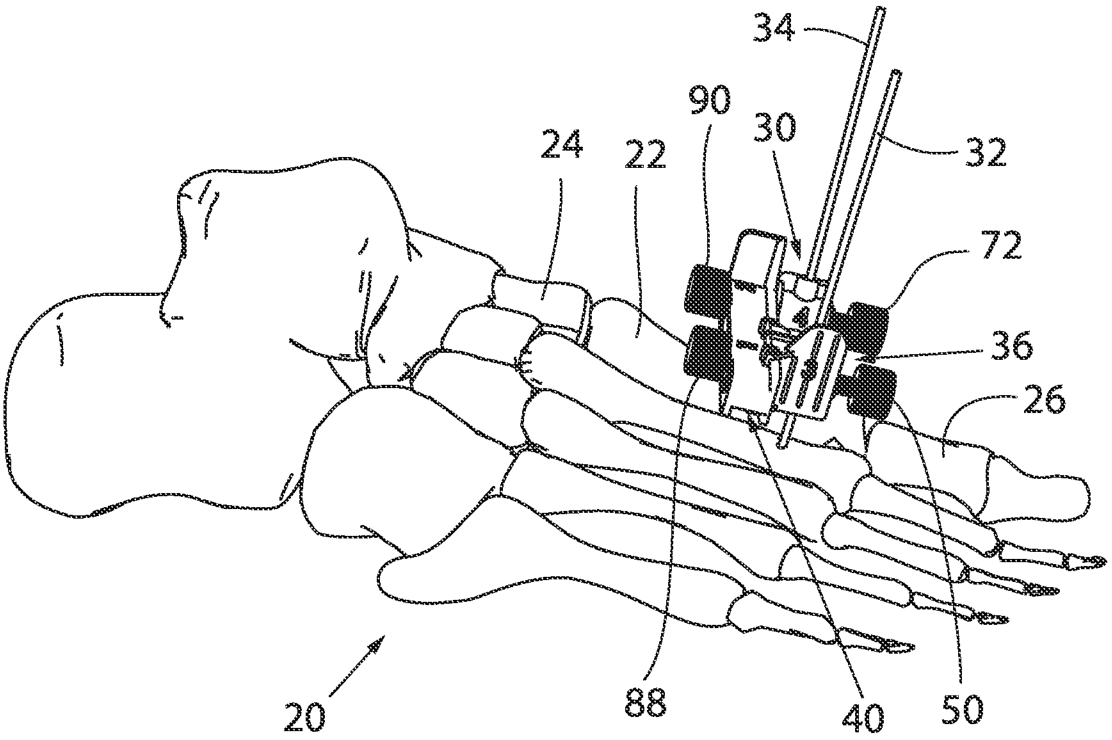
FIG. 16 is a right side elevation view of a foot with a bunion deformity, with the first embodiment of the correction clamp positioned over first and second metatarsal.
Figure 17:
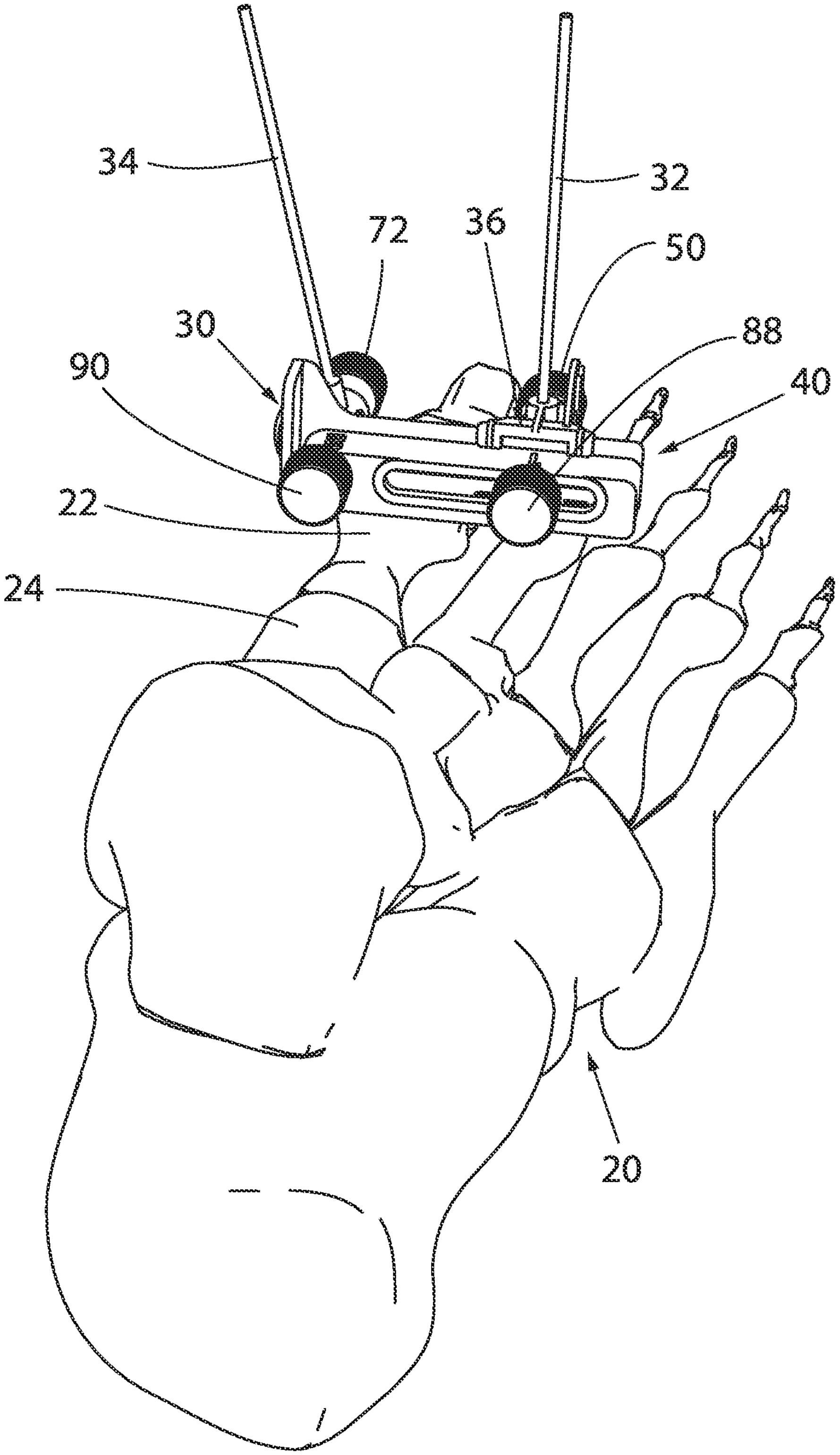
FIG. 17 is a perspective view of the first embodiment of the correction clamp positioned over a foot.
Figure 18:
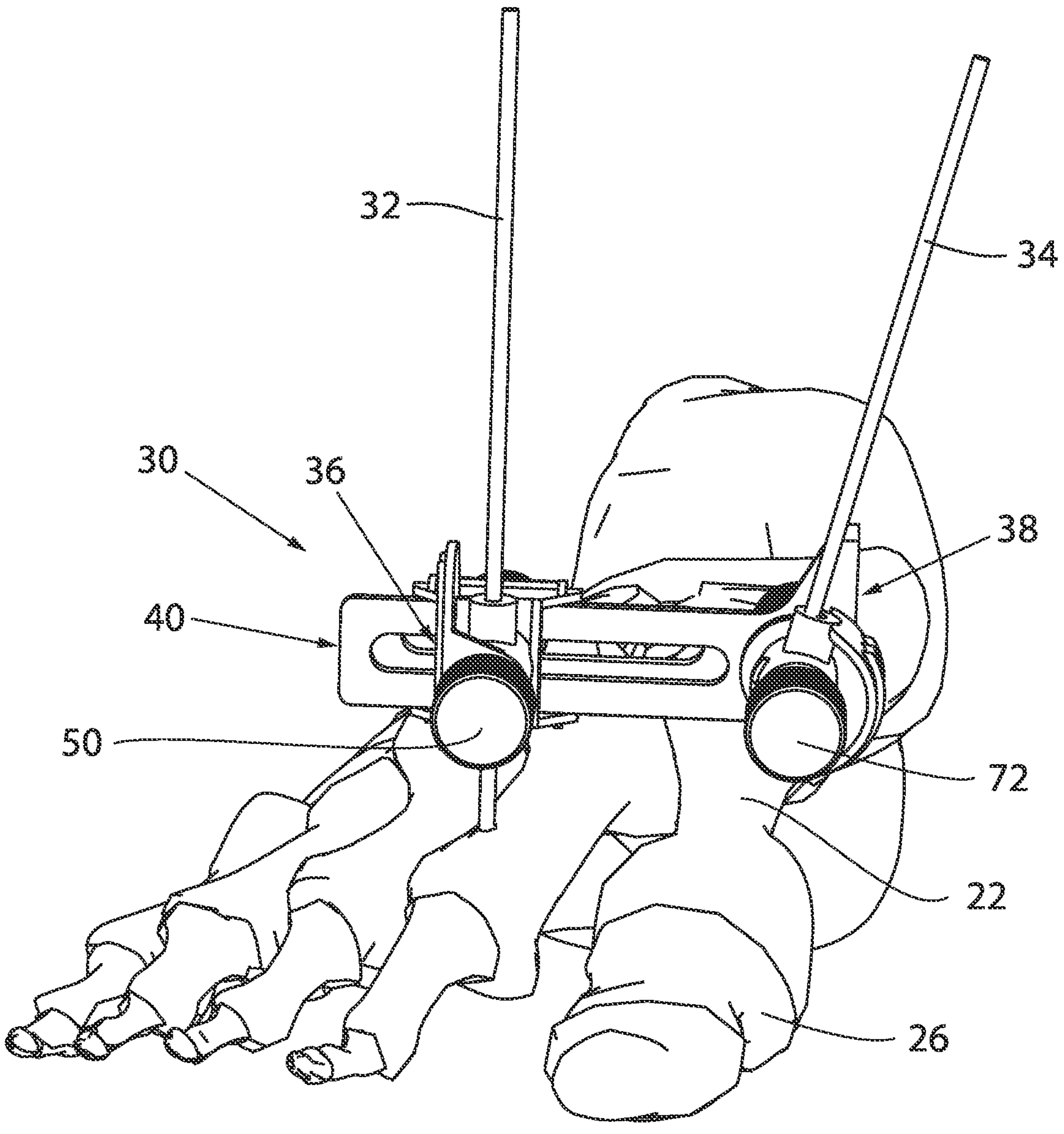
FIG. 18 is an isometric end view of the first embodiment of the correction clamp positioned over the first metatarsal and foot.
Figure 19:
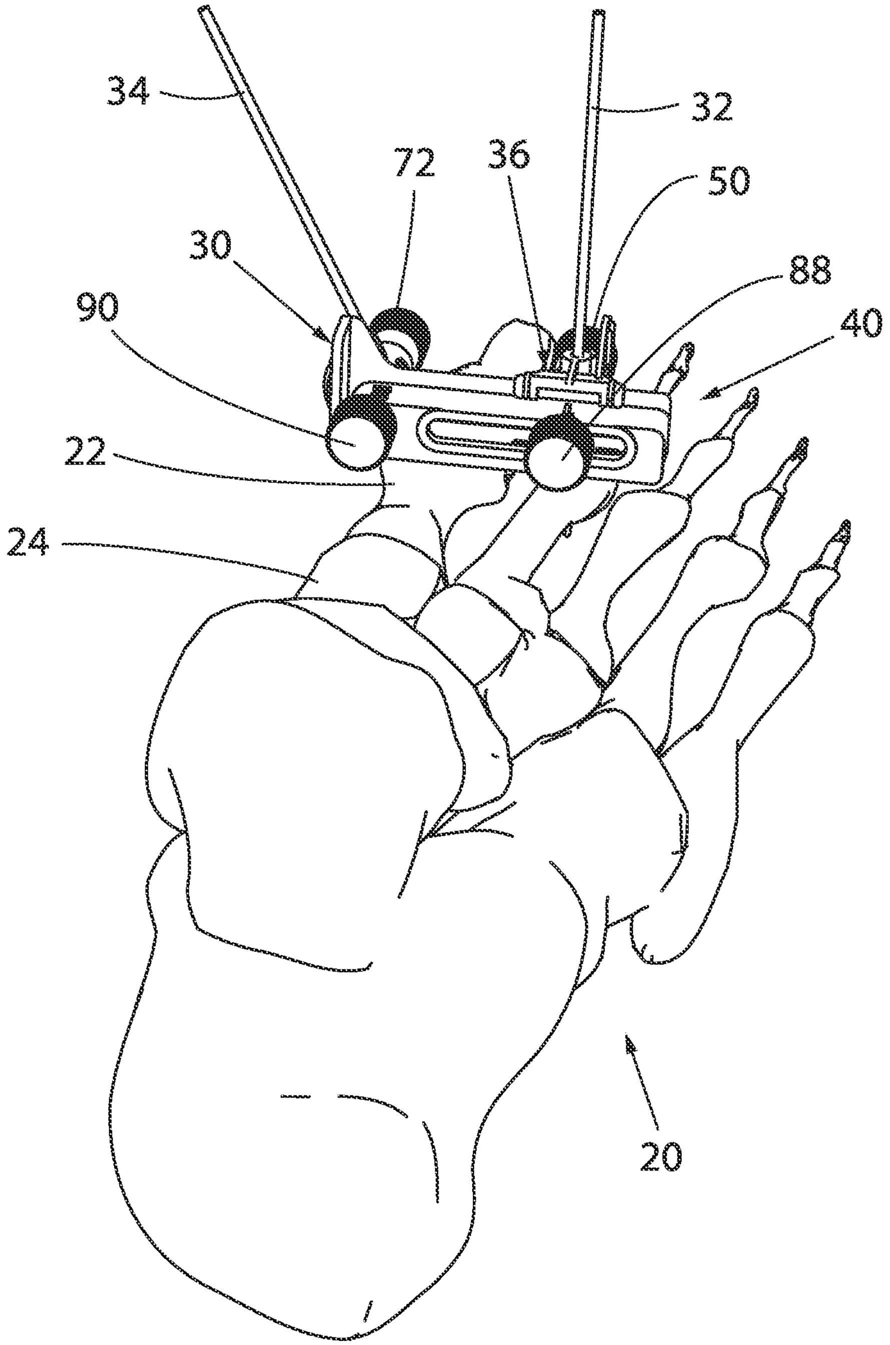
FIG. 19 is an isometric view of a foot with a bunion deformity, with the correction clamp and pins in position, before correction of the deformity.

Next, the second block 38 will be described. The second block 38 includes a body 64 that has a tube 66 with a pin hole opening 68 formed therein that extends through the length of the tube 66. The tube 66 and the pin hole opening 68 extend along a first axis, which will be described herein as a substantially vertical axis based on how it is shown in FIG. 13, but of course the second block 38, as well as the clamp 30, could be oriented in any direction when in use. A screw hole opening 70 also extends through the body 64 of the second block 38, with the screw hole opening 70 extending along a second axis that is substantially perpendicular relative to the first axis. As shown, the second axis is substantially horizontal, such that the screw hole opening 70 extends in the horizontal direction.

The tube 66 is configured to receive the second pin 34 through the pin hole opening 68. The second pin 34 can move freely through the tube 66, otherwise, it can be locked into place, for instance using a locking screw 72 that can be inserted into the screw hole opening 70, after which it can be twisted to either release the second pin 34 or hold it in place.

Additionally, the second block 38 may include a grip section 74 including a textured portion 76, which can be engaged by a user's fingers. Further still, the second block 38 may include an identifier 78, here the number "4", which helps users in terms of identifying the relevant parts and assembly and/or use of the correction clamp 30. The second block 38 may not include an identifier in other embodiments.

Next, the bridge 40 will be described. The bridge 40 includes an elongate body 78. Within the elongate body 78, a slot 80 is shown that extends along a majority of the elongate body 78 from a first end 82 toward a second end 84. The slot 80 allows the first block 36 to be translated towards and away relative to the second block 38 as will be further described below. Additionally, a bridge hole 86 is formed in the second end 84, with a portion of the elongate body 78 separating the bridge hole 86 from the slot 80. Both the slot 80 and the bridge hole 86 are sized to receive additional locking screws 88, 90, as again will further be described below. Further still, the bridge 40 may include a grip section 92 that can be used in conjunction with the grip section 74 of the second block 38 in order to manipulate the various pieces relative to one another as will further be described below. Further still, the bridge 40 may include one or more identifiers 94, 96, here the numbers "1" and "2", which helps users in terms of identifying the relevant parts and assembly and/or use of the correction clamp 30. In other embodiments, the identifiers may be inverted, with identifier 94 being directed to "2" and identifier 96 being "1". In other embodiments the bridge 90 may not include identifiers at all. Further, the bridge 40 may include an upper lip 98 and a lower lip 100 extending from a front face 102 of the bridge 40. Additionally, channel 104 may be located in the bottom of the bridge 40, which in turn forms the lower lip 100. The upper lip 98 and lower lip 100 are dimensioned such that the top guide rail 52 and the bottom guide rail 54 are configured to engage with, and slide along, these lips 98, 100.

As described above, the correction clamp 30 includes a plurality of locking screws, as seen, four locking screws 50, 72, 88, 90. Each of these locking screws 50, 72, 88, 90 are illustrated to be substantially the same, although of course screws having different diameters or operating characteristics could be similarly used. Furthermore, other fasteners configured to releasably attach the various components to one another could similarly be employed.

Whether the illustrated locking screws 50, 72, 88, 90 are used, or other fasteners are, these components allow the first block 36 to be locked and released from translating and/or rotating relative to the bridge 40, and allow the second block 38 to be locked and released from rotating relative to the bridge 40. More specifically, a user of the correction clamp 30 can push or pull on the first block 36 and the second block 38 to translate the first block 36. Once the blocks 36, 38 and associated pins 32, 34 reach a desired location, the locking screws 50, 72, 88, 90 may be tightened in order to hold the first block 36 in place. Thereafter, the locking screws 50, 72, 88, 90 can be loosened to release the first block 36 and allow it to translate. Additionally, the first block 36 and second block 38 are able to rotate relative to the bridge 40. More specifically, locking screws 50, 72, 88, 90 may be tightened or loosed to prevent or enable rotation of the first block 36 or the second block 38.

Additionally, the first block 36 and the second block 38 are both slidably attached to the bridge 40. The bridge 40 may be ratcheted, ridged, or have other features to allow sliding and then locking in place of the first block 36 and the second block 38. The bridge 40 can extend past the first block 36 and the second block 20 if desired or needed. A release button (not shown) or other quick release feature may be used to release the bridge 30 so that it moves freely into the first block 36 or the second block 38, for example if the bridge 40 is ratcheted.

Turning next to FIGS. 3-10, various views are provided of the correction clamp 30, with the first pin 32 and the second pin installed 34 installed. As will be appreciated by one having ordinary skill in the art, the first block 36 can be translated in the slot 80 of the bridge 40. In these figures, the first pin 32 is shown rotated at an angle of approximately 30-degrees relative to the second pin 34. The design of first block 36 and the second block 38 is such that the first pin 32 and the second pin 34 can each be rotated to any desired position.

Next, FIGS. 14-22 show how the correction clamp 30 would be used in surgery on a right foot. The correction clamp 30 could also be made to be suitable for both feet, or with separate right-foot and left-foot versions. These figures show a foot 20 with a first metatarsal 22 and a second metatarsal 28. The correction clamp 30 is shown positioned in place in different views. In the illustrated embodiment, the second block 38 is positioned over the second metatarsal 28, and the second pin 34 is oriented approximately perpendicular to the foot 20 and passes through the second block 38 into the second metatarsal 28. Additionally, the first block 36 is positioned over the first metatarsal 100, and the first pin 32 is angled at approximately 30 degrees relative to the vertical. The first pin 32 passes through the first block 36 and into the first metatarsal 22. In this way, the first pin 32 is configured to allow for rotation of the first metatarsal 22 in the frontal plane. Alternatively, the second block 38 can attach to other undeformed bones of the foot, such as the lesser toe metatarsals or another location, depending on designer and physician preference. Of course, the bridge 40 could be longer than what is shown in the figures when the correction clamp 30 is used with other bones of the foot.

The correction clamp 30 is configured to have the first block 36 attach to an undeformed portion of the foot such as the second metatarsal 28, while second block 38 attaches to a deformed portion of the foot such as the first metatarsal 22, and then allow the first metatarsal 22 to be manipulated by the physician into its proper anatomic location while the correction clamp 30 moves to accommodate this repositioning. The locking screws 50, 72, 88, 90 can be tightened and loosened as needed to allow for appropriate degrees of freedom.

FIGS. 19-22 provide an isometric view of the successive steps of the surgical procedure. First, in FIG. 19, the corrective clamp 30 is positioned on the foot 20, with the second pin 34 in the first metatarsal 22 and the first pin 32 in the second metatarsal 28. The surgeon then prepares the first metatarso-cuneiform joint, after which the first metatarsal 22 can be positioned and rotated freely relative to the second metatarsal 28.

Figure 20:
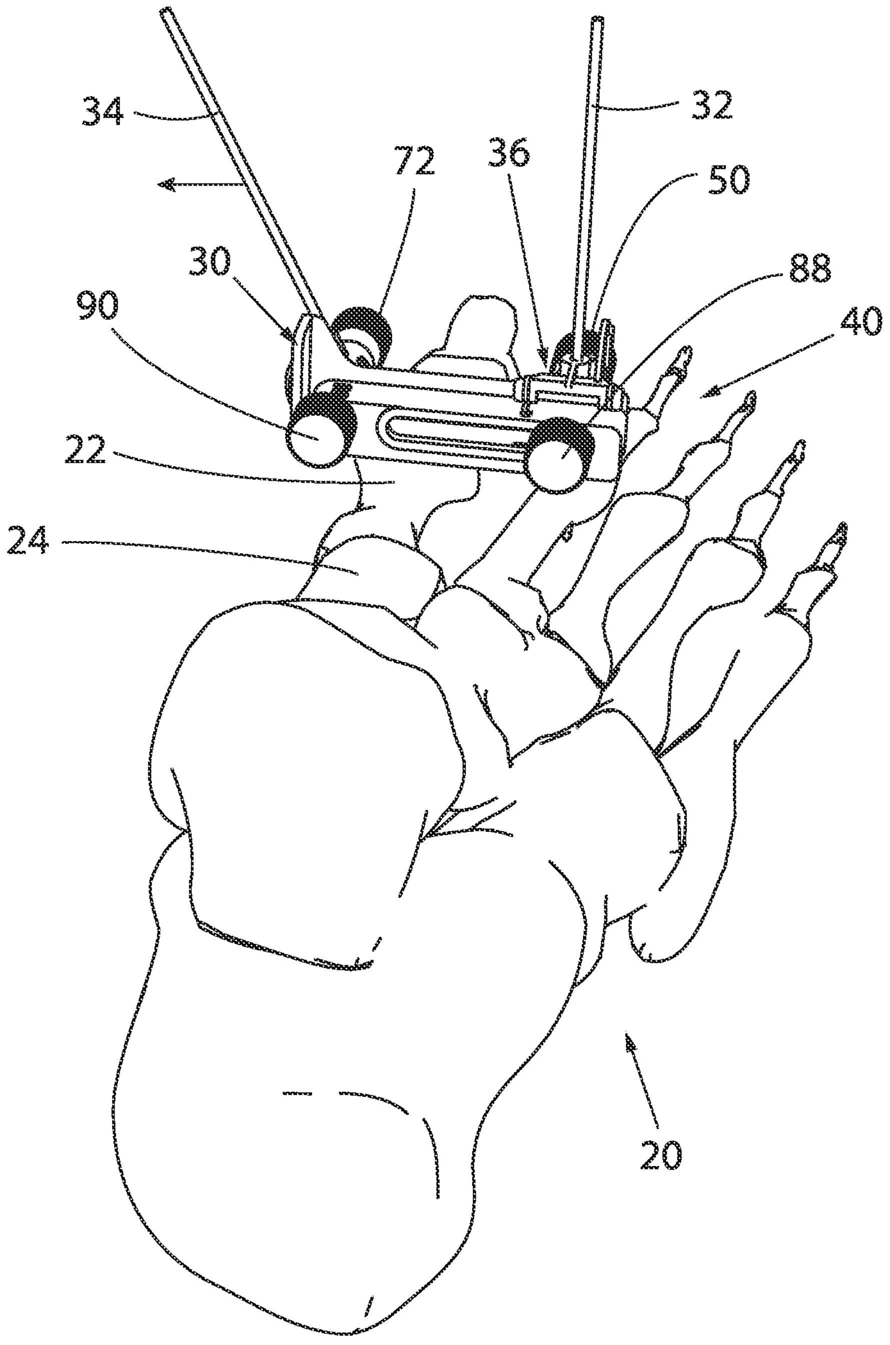
FIG. 20 is an isometric view of a foot with the first metatarsal being manipulated with the correction clamp to begin the correction of the bunion deformity.

Next, FIG. 20 shows the first metatarsal 22 now being straightened to eliminate part of a deformity. The corrective clamp 30 allows second block 38 to be translated away from the first block 36, after the locking screws 72, 90 have been loosened to enable movement.

Figure 21:
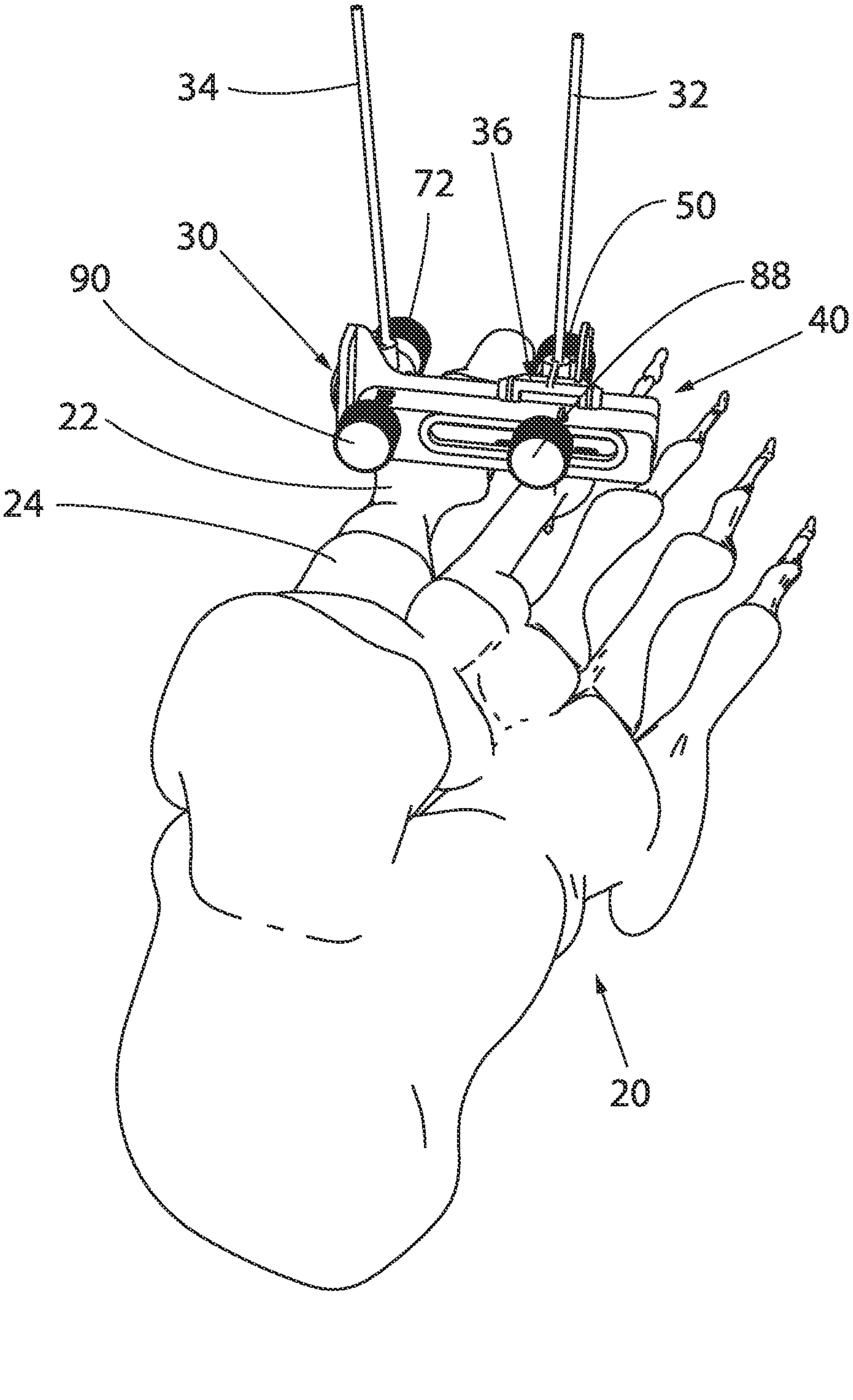
FIG. 21 is an isometric view of a foot with the first metatarsal being shifted towards the second metatarsal using the correction clamp to correct the bunion deformity.

In FIG. 21, the first metatarsal 22 can now be moved into proper anatomical location by pressing the second block 38 towards the first block 36. The first block 36 moves along the bridge 40 in the slot 80. When the first block 36 has moved the desired distance, the locking screws 50 can be tightened to hold the first block 36 in place, and thus hold the first metatarsal 22 in its new position.

Figure 22:
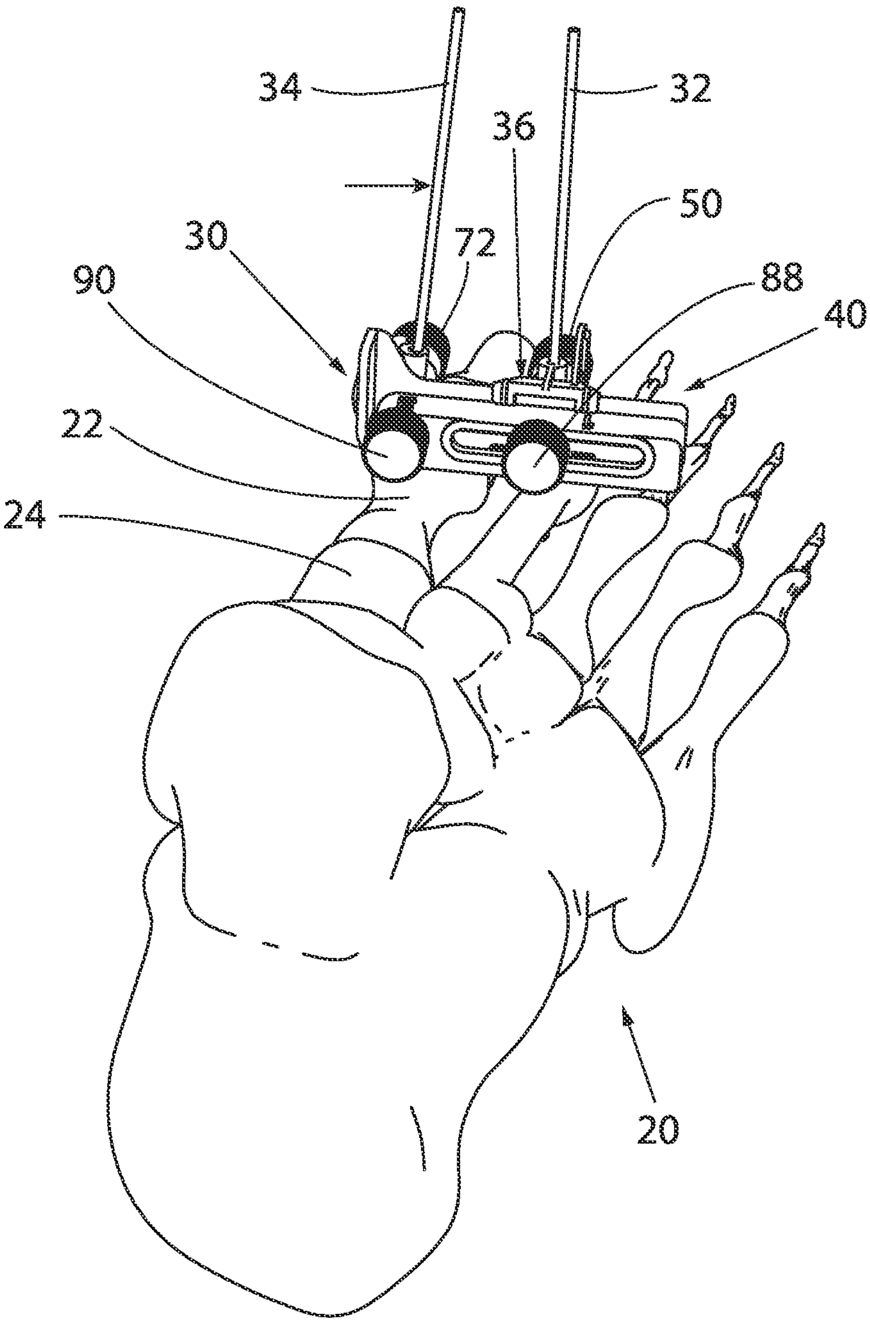
FIG. 22 is an isometric view of a foot with the correction clamp in place and the first pin being rotated towards the second pin such that the bunion deformity is fully corrected.

FIG. 22 shows that one of the locking screw 90 has now been loosened, with the other locking screw 88 remaining tight. Loosening the locking screw 90 allows the second pin 34 to be rotated relative to first pin 32. Since the second pin 34 passes into the first metatarsal 22, in this way the first metatarsal 22 is also rotated relative to the second metatarsal 24. The locking screw 90 can be tightened when the desired correction is achieved.

The steps described above and shown in FIGS. 19-22 can be iterated any number of times, to properly position the two metatarsals. The locking screws 50, 72, 88, 90 can be loosened and tightened as needed, to allow for relative motion of the two metatarsals. The corrective clamp 30 is capable of correcting the abnormal metatarsal/foot deformity and holding the two metatarsals in the corrected position until the surgeon places permanent fixation.

The correction clamp 30 and associated components can be packaged together with a first pin 32 and a second pin 34, as well as other instruments in a surgical kit. The kit can be presented in the operating room as a pre-sterilized kit, or non-sterile. The kit can include common fixation mechanisms such as nitinol staple, orthopedic screws, or a plate with screws.

Turning next to FIGS. 23-28, another embodiment of the inventive correction clamp 130, where similar components are labeled with the same reference numbers as those for the clamp 30 increased by 100. Many of the components of the clamp 30 and the clamp 130 are identical or substantially identical, including for instance the second block 138, the bridge 140, and the pins 132, 134, with important points of distinction noted below.

Figure 23:
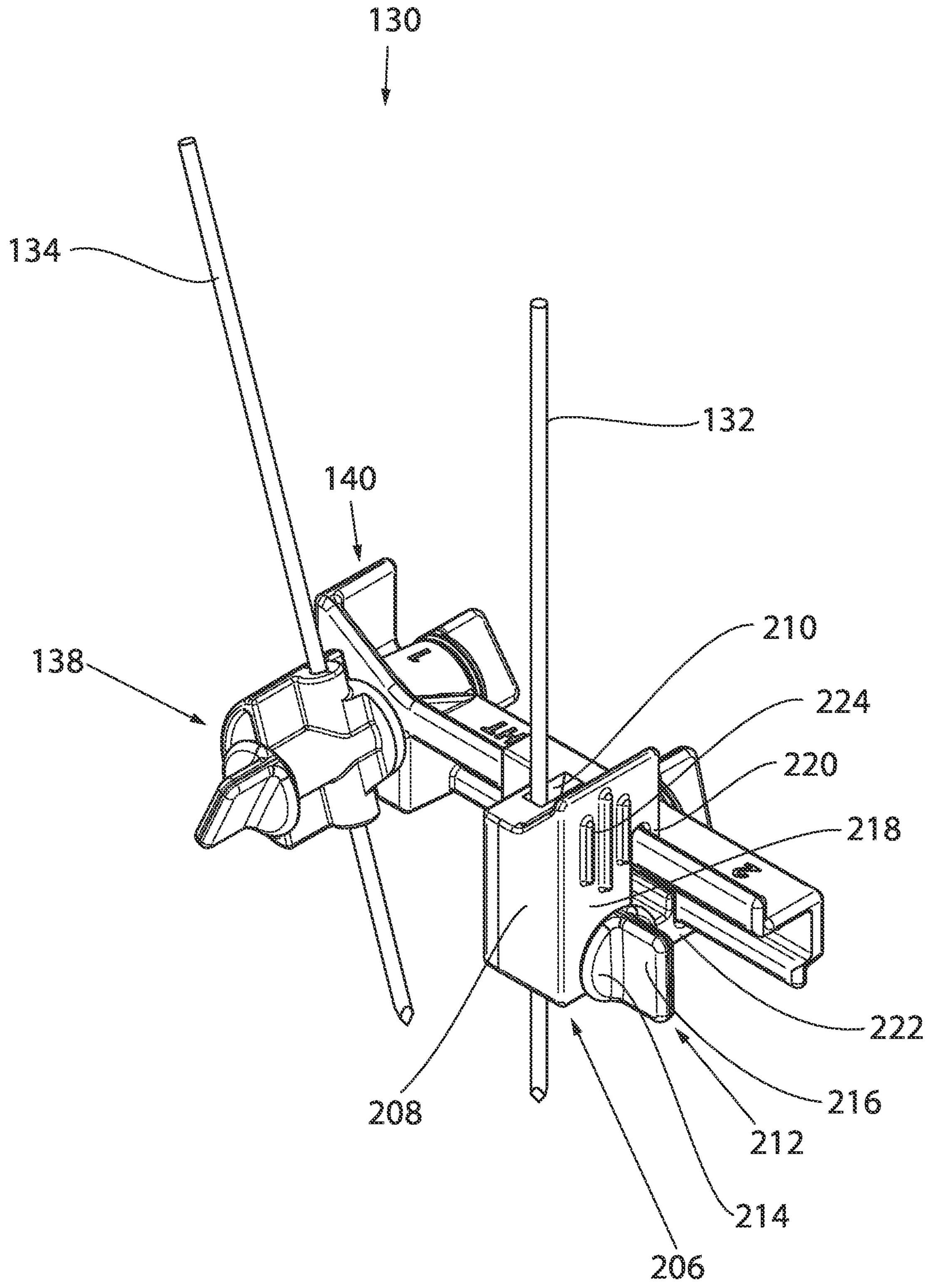
FIG. 23 is an isometric view of a second embodiment of an inventive corrective clamp with pins extending therethrough.
Figure 24:
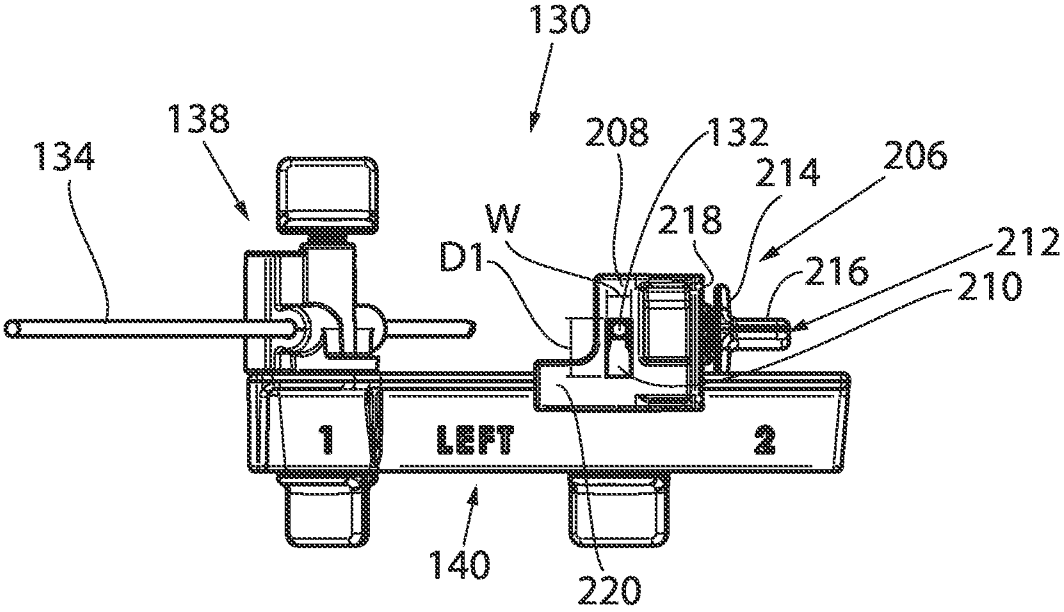
FIG. 24 is a top plan view of the corrective clamp of FIG. 23.
Figure 25:
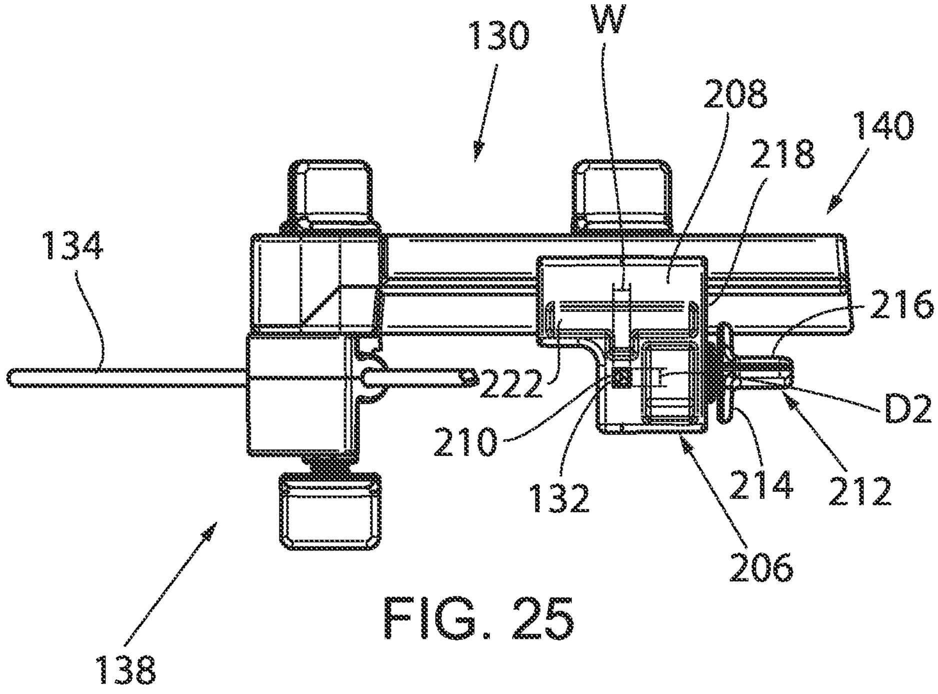
FIG. 25 is a bottom plan view of the corrective clamp of FIGS. 23 and 24.
Figure 26:
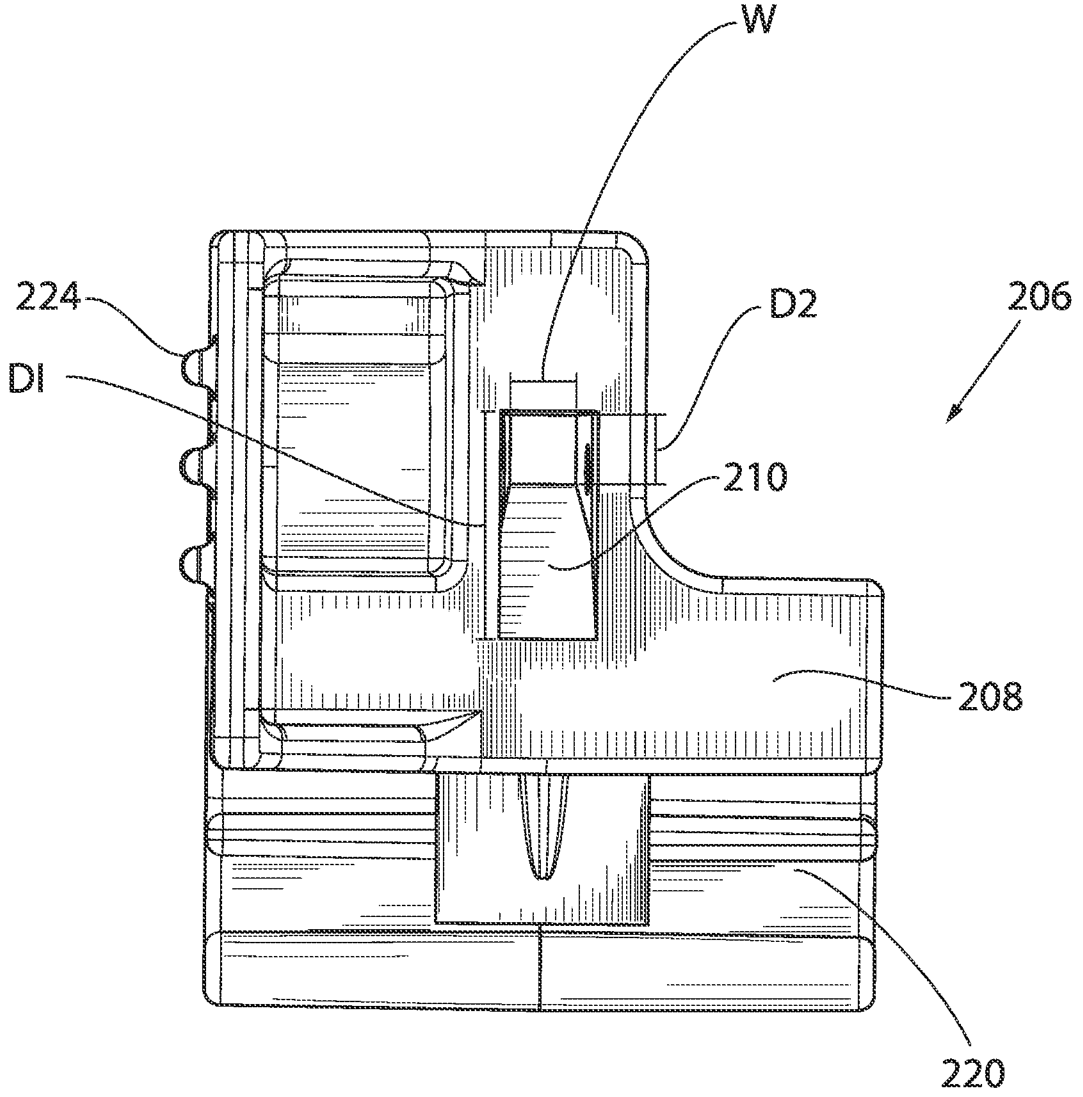
FIG. 26 is a top plan view of a first block of the correction clamp of FIGS. 23-25.

However, the clamp 130 has a different first block 206. The first block 206 includes a body 208 that has a channel 210 extending therethrough. As shown, the channel 210 extends along a first axis, which will be described herein as a substantially vertical axis based on how it is shown in FIG. 23, but of course the first block 206, as well as the clamp 130, could be oriented in any direction when in use. The channel 210 has was a width W that is slightly larger than the width of the pin 132 to enable the pin 132 to securely fit therein while minimizing side-to-side movement within the channel 210. The channel 210 may be tapered in shape, such that it has a depth D1 at the top (see FIGS. 23, 24, and 26) that is greater than the depth D2 at the bottom (see FIG. 25) which is slightly larger than the depth of the pin 132. This configuration allows the pin 132 to remain in substantially the same location at the bottom of the channel 210 of the first block 206, while being able to move forward and backward about the top of the channel 210. The shape of the channel 210 allows a user to manipulate movement of the pin 132 relative to the first block 206 with a greater degree of freedom. Alternatively, the channel 210 may have the same depth for the entire channel 210. After the first block 206 and second block 138 are positioned over the first and second bones (See FIG. 27), the user can rotate pin 132 relative to the first block 206 within the channel 210, before locking it in place with a locking screw 212, which will further be described below. In this way, the user can obtain even better orientation of the clamp 130 relative to two bones in comparison to the clamp 30.

Additionally, the first block 206 includes a locking screw 212. The design of locking screw 212 is different from locking screw 50, used with the first block 36. More specifically, the locking screw 212 includes a circular base 214 that abuts the body 208 of the first block 206 and a tab 216 that extends away from the base 214. This configuration allows a physician to grasp and twist the locking screw 212, and more specifically the tab 216, more easily than screw 50. As shown, the remaining locking screws associated with the clamp 130 have a similar structure as locking screw 212. Of course, any screw associated with clamp 30 or clamp 130 may also feature locking screws having a similar structure as the locking screw 212. In addition, the locking screw 212 is located on the first block 206 at a different location, coming from a side surface 218, that permits better visibility of the surgical site, while also reducing the probability of interference of the user with pin 132.

Additionally, top and bottom guide rails 220, 222 are provided that extend from the body 208 of the first block 206. Again, use of the words "top" and "bottom" are used relative to what is shown in FIG. 23, although the components could be used in other orientations. These guide rails 220, 222 are configured to secure the first block 206 to the bridge 140 and enable movement of the first block 206 relative to the bridge 140 as described above. Further still, the first block 206 may include a grip section 224, which can be engaged by a user's fingers.

Figure 27:
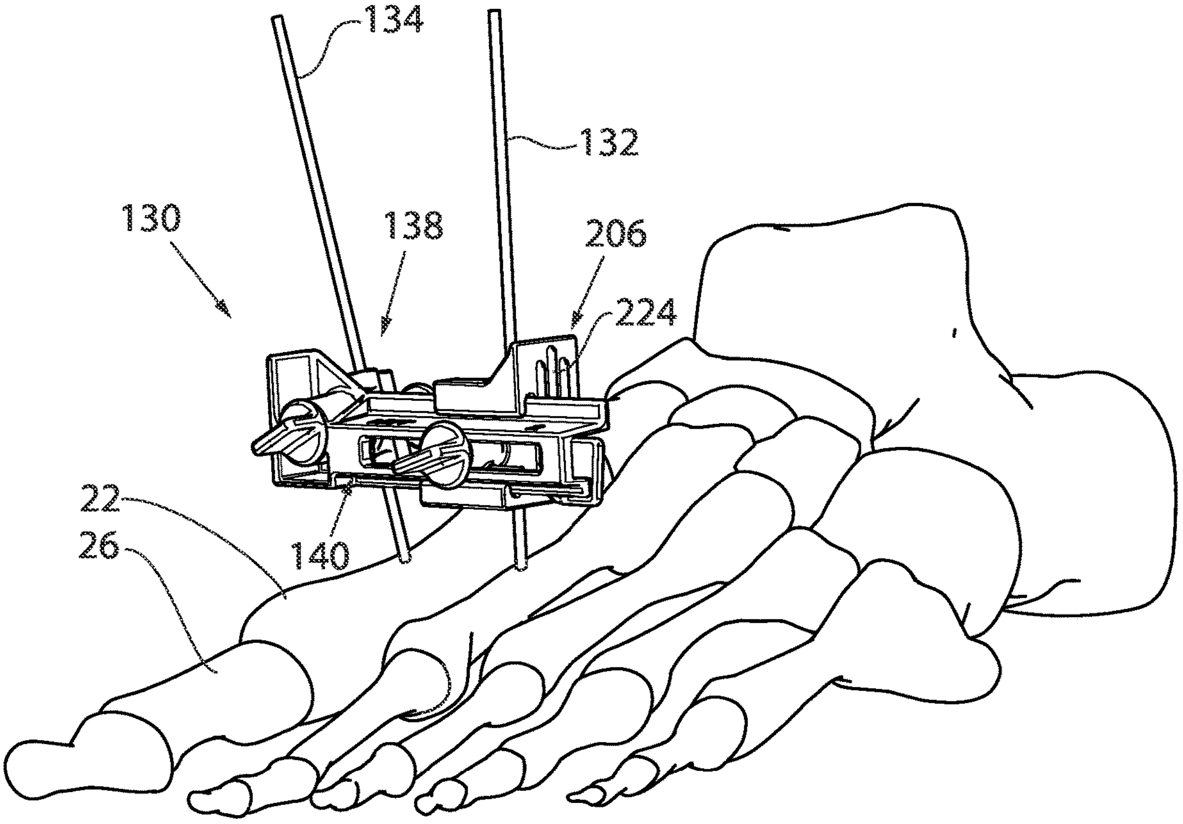
FIG. 27 is a perspective view of a second embodiment of the correction clamp positioned over a first and second metatarsal.

FIG. 27 shows the second embodiment of the clamp 206 positioned over a first and second metatarsal. The new location of locking screw 212 now allows motion of the pin 132 in channel 210 with less chance of interference between the user and the pin 132. Additionally, the shape of the channel 210 permits additional orientation of clamp 206 relative to the two bones being addressed in surgery. Similar to the clamp 30, the clamp 130 is locked in place with locking screws.

Figure 28:
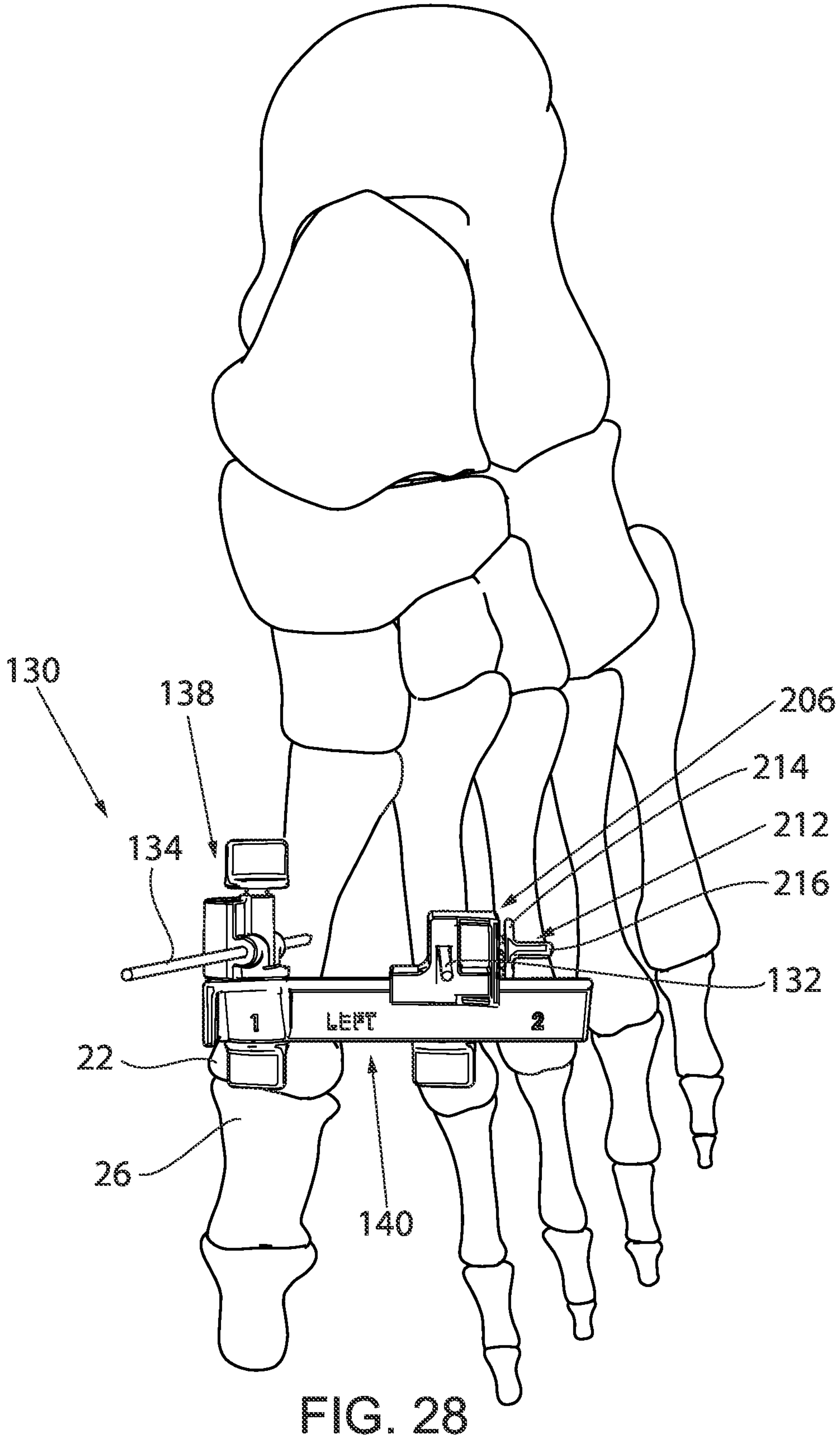
FIG. 28 is an isometric end view of a second embodiment of the correction clamp in place positioned over the first metatarsal and foot.

FIG. 28 shows an top view of the second embodiment of a clamp 130, positioned over a first and second metatarsal. The rectangular shape of the channel 210 on the first block 206 is seen, and allows additional positioning freedom for the clamp 130 relative to the two bones.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. For example, any of the specific aspects of any of the described embodiments could similarly be used with any of the other embodiments. Furthermore, while specific materials have been described, it should be known that any materials could used to create any of the described drapes. For instance, materials may be chosen based on any number of criteria, including costs, availability, and various sterility properties. Moreover, as described above, the individual components need not be formed in the disclosed shapes, or assembled in the disclosed configuration, but could be provided in virtually any shape, and assembled in virtually any configuration. Further, any of the components can be manufactured with one another or be separately manufactured and later assembled. Furthermore, all the disclosed features of each disclosed embodiment can be combined with, or substituted for, the disclosed features of every other disclosed embodiment except where such features are mutually exclusive. Figures are not to scale, and some features are exaggerated to show details of particular features or method steps. Further still, some of the tools described above may be reusable, while others may be disposable.

It is intended that the appended claims cover all such additions, modifications and rearrangements. Expedient embodiments of the present invention are differentiated by the appended claims.

What is claimed is:

1. A method of performing a medical procedure comprising the steps of:

inserting a first pin through a second metatarsal;

inserting the first pin through a first block associated with a correction clamp;

inserting a second pin through a first metatarsal;

inserting the second pin through a second block associated with the correction clamp;

creating a corrective cut in one or more of a bone and a joint;

manipulating the second pin to move the second block and the first metatarsal relative to the second metatarsal;

manipulating the first pin relative to a channel extending through the first block;

reaching a desired location of the first metatarsal; and securing the first metatarsal in place.

2. The method of performing a medical procedure of claim 1, further comprising the steps of:

sliding the first block relative to a bridge associated with the correction clamp; and rotating the second block relative to the bridge.

3. The method of performing a medical procedure of claim 2, further comprising the steps of:

sliding the first block relative to a slot formed in the bridge; and rotating the second block about a bridge hole formed in the bridge.

4. The method of performing a medical procedure of claim 2, further comprising the steps of:

securing the first block in place relative to the bridge using a first locking screw; and securing the second block in place relative to the bridge using a second locking screw.

5. The method of performing a medical procedure of claim 1, further comprising the steps of:

inserting the first pin through the first block; and inserting the second pin through the second block.

6. The method of performing a medical procedure of claim 1, further comprising the steps of:

pressing the second pin towards the first pin; and moving the first metatarsal to the desired location.

7. The method of performing a medical procedure of claim 6, further comprising the steps of:

releasably securing the first block into place relative to a bridge associated with the corrective clamp once the first metatarsal is in the desired location; and releasably securing the second block into place relative to the bridge associated with the corrective clamp once the first metatarsal is in the desired location.

* * * * *